(12) United States Patent
Weaver et al.

(10) Patent No.: US 7,597,692 B2
(45) Date of Patent: *Oct. 6, 2009

(54) MICROSCISSION PROCESSES AND PROCEDURES

(75) Inventors: James C. Weaver, Sudbury, MA (US); R. Rox Anderson, Lexington, MA (US); Terry O. Herndon, Carlisle, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 915 days.

This patent is subject to a terminal disclaimer.

(21) Appl. No.: 10/800,587

(22) Filed: Mar. 15, 2004

(65) Prior Publication Data

US 2004/0204700 A1 Oct. 14, 2004

Related U.S. Application Data

(63) Continuation-in-part of application No. 09/878,155, filed on Jun. 7, 2001, now Pat. No. 6,706,032.

(60) Provisional application No. 60/209,985, filed on Jun. 8, 2000.

(51) Int. Cl.
*A61M 31/00* (2006.01)

(52) U.S. Cl. .............................. 604/500; 604/68; 604/22

(58) Field of Classification Search .................. 604/500, 604/501, 19, 22, 28, 68–70; 606/167, 184–186; 128/898

See application file for complete search history.

(56) References Cited

U.S. PATENT DOCUMENTS 5,003,987 A 4/1991 Grinwald ..................... 128/734

(Continued)

FOREIGN PATENT DOCUMENTS

EP 0 417 290 3/1991

(Continued)

OTHER PUBLICATIONS

Terry O Herndon et al., Transdermal microconduits by microscission for drug delivery and sample acquisition, BMC Medicine 2004, 2:12, Apr. 19, 2004.

(Continued)

*Primary Examiner*—Kevin C Sirmons
*Assistant Examiner*—Bhisma Mehta
(74) *Attorney, Agent, or Firm*—Thomas J. Engellenner; Rory P. Pheiffer; Nutter McClennen & Fish LLP

(57) ABSTRACT

The present invention relates to microscission methods and devices used for the manipulation or modification of the body tissue by the formation of microconduits in a tissue. The term "microconduit" refers to a small opening, channel, or hole into, or through, a tissue, that allows transfer of materials by liquid flow, and by electrophoresis, the microconduit being formed upon impact of a plurality of accelerated microparticles with the surface of the tissue. This process of "microscission" comprises forming at least one microconduit in tissue including the steps of: accelerating a plurality of microparticles to a velocity that causes the microparticles to penetrate a region of tissue surface upon impingement of the microparticles on the tissue surface; and directing the microparticle towards the region of tissue surface, thereby causing the microparticles to penetrate the tissue and form a microconduit in the tissue.

26 Claims, 4 Drawing Sheets

U.S. PATENT DOCUMENTS

| | | | |
|---|---|---|---|
| 5,019,034 A | 5/1991 | Weaver et al. | 604/20 |
| 5,389,069 A | 2/1995 | Weaver | 604/21 |
| 5,547,467 A | 8/1996 | Pliquett et al. | 604/20 |
| 5,630,796 A | 5/1997 | Bellhouse et al. | 604/49 |
| 5,667,491 A | 9/1997 | Pliquett et al. | 604/50 |
| 5,688,233 A | 11/1997 | Hofmann et al. | 604/20 |
| 5,749,847 A | 5/1998 | Zewert et al. | 604/49 |
| 5,885,211 A | 3/1999 | Eppstein et al. | 600/309 |
| 5,911,223 A | 6/1999 | Weaver et al. | 128/898 |
| 5,947,956 A * | 9/1999 | Karell | 606/9 |
| 5,983,131 A | 11/1999 | Weaver et al. | 604/20 |
| 6,010,478 A * | 1/2000 | Bellhouse et al. | 604/70 |
| 6,022,316 A | 2/2000 | Eppstein et al. | 600/309 |
| 6,085,115 A | 7/2000 | Weaver et al. | 600/509 |
| 6,142,939 A | 11/2000 | Eppstein et al. | 600/309 |
| 6,706,032 B2 | 3/2004 | Weaver et al. | |

FOREIGN PATENT DOCUMENTS

| | | |
|---|---|---|
| WO | WO 97/04832 | 2/1997 |
| WO | WO 97/07734 | 3/1997 |
| WO | WO 00/03758 | 1/2000 |
| WO | WO 01/93947 A1 | 12/2001 |

OTHER PUBLICATIONS

Langer, R., "Drug Delivery and Targeting.," *Nature*, 392:S5-S10 (1998).

Elias, P.M., et al. "Percutaneous Transport in Relation to Stratum Corneum Structure and Lipid Composition," *J. Invest. Dermatol.*, 76(4): 297-301 (1981).

Elias, P.M., and Menon, G.K., "Structural and Lipid Biochemical Correlates of the Epidermal Permeability Barrier," *Adv. Lipid Res.*, 24: 1-26 (1991).

Zewert, T.E., et al., "Creation of Transdermal Pathways for Macromolecule Transport by Skin Electroporation and a Low Toxicity, Pathway-Enlarging Molecule," *Bioelectrochem. and Bioenerget.*, 49:11-20 (1999).

Ilic, L., et al., "Electrochemical Creation of Microconduits in Full-Thickness Human Skin for Transdermal Drug Delivery by Pressure-Driven Flow," *Proc. Internat. Symp. on Controlled Release of Bioact. Materials*, Controlled Release Society, 26:178-179 (1999).

Ilic, L., et al., "Spatially Constrained Skin Electroporation with Sodium Thiosulfate and Urea Creates Transdermal Microconduits," *J. Control. Release*, 61:185-202 (1999).

Yamashita, N., et al., "Scanning Electron Microscopic Evaluation of the Skin Surface after Ultrasound Exposure," *The Anatomical Record*, 247: 455-461 (1997).

Tachibana, K., and Tachibana, S., "Transdermal Delivery of Insulin by Ultrasonic Vibration," *J. Pharm. Pharmacol.*, 43(4):270-271 (1991).

Mitragotri, S., et al., "Ultrasound-Mediated Transdermal Protein Delivery," *Science*, 269: 850-853 (1995).

Mitragotri, S., et al., "Determination of Threshold Energy Dose for Ultrasound-Induced Transdermal Drug Transport," *J. Controlled Release*, 63:41-52 (2000).

Jacques, S.L., et al., "Controlled Removal of Human Stratum Corneum by a Pulsed Laser," *J. Invest. Dermatol.*, 88(1):88-93 (1987).

Nelson, J.S., et al., "Mid-Infrared Laser Ablation of Stratum Corneum Enhances in Vitro Percutaeous Transport of Drugs," *J. Invest. Dermatol.*, 97(5):874-879 (1991).

Eisenbraun, M.D., et al., "Examination of Parameters Affecting the Eliciation of Humoral Immune Responses by Particle Bombardment-Mediated Genetic Immunization," *DNA and Cell Biology*, 12(9):791-797 (1993).

Macklin, M.D., et al., "Immunization of Pigs with a Particle-Mediated DNA Vaccine to Influenza A Virus Protects Against Challenge with Homologous Virus," *J. of Virology*, 72(2):1491-1496 (1998).

Smith, A., et al., "Fluorescein Kinetics in Interstitial Fluid Harvested from Diabetic Skin During Fluorescein Angiography: Implications for Glucose Monitoring," *Diabetes Tech. & Therapeut.*, 1(1): 21-27 (1999).

Cullander, C., "What Are the Pathways of Iontophoretic Current Flow Through Mammalian Skin?" *Adv. Drug Delivery Rev.*, 9(2/3):119-135 (1992).

Inada, H., et al., "Studies on the Effects of Applied Voltage and Duration on Human Epidermal Membrane Alteration/recovery and the Resultant Effects upon Iontophoresis," *Pharm. Res.*, 11(5):687-697 (1994).

Green, P.G., "Iontophoretic Delivery of Peptide Drugs," *J. Controlled Release*, 41:33-48 (1996).

Merino, V., et al., "Transdermal Therapy and Diagnosis by Iontophoresis," *TIBTech.*, 15:288-290 (1997).

Dinh, S.M., et al., "Upper and Lower Limits of Human Skin Electrical Resistance in Iontophoresis," *AIChE J.*, 39(12):2011-2018 (1993).

Monteiro-Riviere, N.A., et al., "Identification of the Pathway of Iontophoretic Drug Delivery: Light and Ultrastructure Studies Using Mercuric Chloride in Pigs," *Pharm. Res.*, 11(2):251-256 (1994).

Langkjaer, L., et al., "Iontophoresis of Monomeric Insulin Analogues In Vitro: Effects of Insulin Charge and Skin Pretreatment," *J. Control. Release*, 51:47-56 (1998).

Chizmadzhev, Y., et al., "Electrical Properties of Skin at Moderate Voltages: Contribution of Appendageal Macropores," *Biophys. J.*, 74:843-856 (1998).

Prausnitz, M.R., et al., "Electroporation of Mammalian Skin: A Mechanism to Enhance Transdermal Drug Delivery," *Proc. Nat. Acad. Sci. USA*, 90:10504-10508 (1993).

Prausnitz, M. R., et al., "Methods for in Vivo Tissue Electroporation Using Surface Electrodes," *Drug Delivery*, 1(2):125-131, (1993).

Gallo, S.A, et al., "Characterization of Electric-Pulse-Induced Permeabilization of Porcine Skin Using Surface Electrodes," *Biophysical Journal*, 72: 2805-2811 (1997).

Vanbever, R., et al., "In vivo Noninvasive Evaluation of Hairless Rat Skin after High-Voltage Pulse Exposure," *Skin Pharmacol. Appl. Skin Physiol.*, 11:23-34 (1998).

Vanbever, R., et al., "Transdermal Delivery of Fentanyl: Rapid Onset of Analgesia Using Skin Electroporation," *J. Controlled Release*, 50:225-235 (1998).

Chen, T., et al., "Skin Electroporation Causes Molecular Transport Across the Stratum Corneum Through Localized Transport Regions," *J. Invest. Dermatol. Symposium Proceedings*, 3:159-165 (1998).

Chen, T., et al., "Skin Electroporation: Rapid Measurements of the Transdermal Voltage and Flux of Four Fluorescent Molecules Show a Transition to Large Fluxes near 50 V," *J. of Pharm. Sci.*, 87(11):1368-1374 (1998).

VanBever, R., et al., "Comparison of the Effects of Short, High-voltage and Long, Medium-Voltage Pulses on Skin Electrical and Transport Properties," *J. Controlled Release*, 69:35-47, (1999).

Zewert, T.E., et al., Transdermal Transport of DNA Antisense Oligonucleotides by Electroporation. *Biochem. Biophy. Res. Comm.*, 212(2): 286-292 (1995).

Prausnitz, M.R., et al., "Transdermal Delivery of Heparin by Skin Electroporation," *Biotechnology*, 13: 1205-1209 (1995).

Heise, H.M., "Non-Invasive Monitoring of Metabolites Using Near Infrared Spectroscopy: State of the Art," *Horm. Metab. Res.*, 28:527-534 (1996).

Fischer, U., et al., "Assessment of Subcutaneous Glucose Concentration: Validation of the Wick Technique as a Reference for Implanted Electrochemical Sensors in Normal and Diabetic Dogs," *Diabetologia*, 30(12):940-945 (1987).

Quan, K.M., et al., "Glucose Determination By a Pulsed Photoacoustic Technique: An Experimental Study Using A Gelatin-Based Tissue Phantom," *Phys. Med. Biol.*, 38(12):1911-1922, (1993).

Tamada, J.A., et al., "Measurement of Glucose in Diabetic Subjects Using Noninvasive Transdermal Extraction," *Nature Medicine*, 1(11):1198-1202 (1995).

Ito, N., et al., "Transcutaneous Blood Glucose Monitoring System Based on ISFET Glucose Sensor and Studies on Diabetic Patients," *Frontiers Med. Biol. Engng.*, 6(4):269-280 (1995).

Berger, A.J., "Feasibility of Measuring Blood Glucose Concentration by Near-infrared Raman Spectroscopy," *Spectochim. Acta*, 53(Part A) :287-292 (1997).

Schiffman, et al., "Airway Humidification in Mechanically Ventilated Neonates and Infants: A Comparative Study of a Heat and Moisture Exchanger vs. a Heated Humidifier Using a New Fast-response Capacitive Humidity Sensor," *Crit. Care Med.* 25 (10) : 1755-1760 (1997).

Ohhashi, et al., "Human Perspiration Measurement," *Physiol. Meas.* 19(4): 449-461 (1998).

Pliquett, U.F., et al. "Imaging of Fluorescent Molecules and Small Ion Transport Through Human Stratum Corneum During High-Voltage Pulsing: Localized Transport Regions Are Involved," *J. Biophys. Chem.*, 58:185-204, (1996).

Prausnitz, M.R., et al., "Imaging Regions of Transport Across Human Stratum Corneum During High Voltage and Low Voltage Exposures," *J. Pharm. Sci.*, 85(12) :1363-1370, (1996).

Weaver, J.C., et al. "Theory of Electrical Creation of Aqueous Pathways Across Skin Transport Barriers," *Advanced Drug Delivery Reviews*, 35(1):21-39, (1999).

Gowrishankar, T.R., et. al., "Spatially Contrained Localized Transport Regions Due to Skin Electroporation," *J. controlled Release*, 60(1):101-110 (1999).

Hikima, T., et al., "Effect of Ultrasound Application on Skin Metabolism of Prednisolone 21-Acetate," *Pharm. Res.*, 15(11):1680-1683 (1998).

Wu, J., et al., "Defects Generated in Human Stratum Corneum Specimens by Ultrasound," *Ultrasound in Med. & Biol.* 24(5):705-710 (1998).

Henry, S., et al., "Microfabricated Microneedles: A Novel Approach to Transdermal Drug Delivery," *J. Pharm. Sci.* 87(8):922-925 (1998).

Miyajima, et al., "Effect of Polymer/Basic Drug Interaction on the Two-Stage Diffusion-Controlled Release from a Poly(L-lactic Acid) Matrix," *J. Controlled Rel.* 61(3) :295-304 (1999).

Simon, L.D., et al., "Mechanisms Controlling Diffusion and Release of Model Proteins Through and From Partially Esterified Hyaluronic Acid Membranes," *J. Controlled Rel.* 61(3):267-279 (1999).

Prestwich, G.D., et al., "Controlled Chemical Modification of Hyaluronic Acid: Synthesis, Applications, and Biodegradation of Hydrazide Derivatives," *J. Control. Release* 53:93-103 (1998).

Koo, T-W., et al., "Reagentless Blood Analysis by Near-Infrared Raman Spectroscopy," *Diabetes Tech. Therapeut.*, 1(2):153-157 (1999).

Berger, A.J., et al., "Multicomponent Blood Analysis by Near-Infrared Raman Spectroscopy," *Appl. Optics* 38(13):2916-2926 (1999).

Longridge, D.J., et al., Effects of Payload Per Unit Area on Dermal Powderject® Delivery of Testosterone to Conscious Rabbits, *Proceed. Int'l. Symp. Control. Rel. Bioact. Mater.*, 25:595-596 (1998).

Uchida, M., et al., "Transdermal Microparticle Delivery by a Supersonic Helios™ Gun System," *Proceed. Int'l. Symp. Control. Rel. Bioact. Mater.*, 25:575-576 (1998).

Sage, B.H., Jr., "Iontophoresis" *CRC Press, Inc., Chapter 15.1 Percutaneous Penetration Enhancers* 351-368 (1995).

Weaver, J.C., and Langer, R., "Electrochemical Creation of Large Aqueous Pathways: an Approach to Transdermal Drug Delivery," *Progress in Dermatology*, 33:1-10 (1999) .Nov. 26, 2001.

McAllister, D.V., et al., "Microfabricated Microneedles: A Novel Approach to Transdermal Drug Delivery," *Proceed. Int'l. Symp. Control. Rel. Bioact. Mater.*, 25:30-31 (1998).

Scott, E.R., et al., "Direct Imaging of Ionic Pathways in Stratum Corneum Using Scanning Electrochemical Microscopy," *Solid State Ionics*, 53-56 (Part 1) :176-183 (1992).

Weaver, J.C. and Langer, R. "Electrochemical Creation of Large Aqueous Pathways: an Approach to Transdermal Drug Delivery," Progress in Dermatology, 33: 1-10 (1999) Nov. 26, 2001.

\* cited by examiner

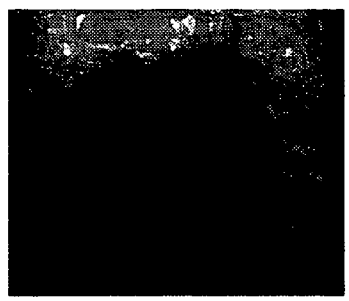
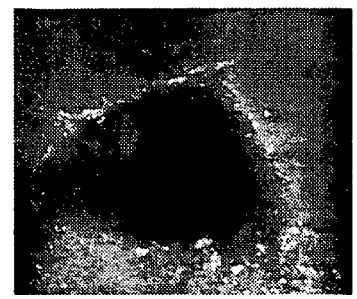
0 µm
FIG. 5A
FIG. 5B
FIG. 5C
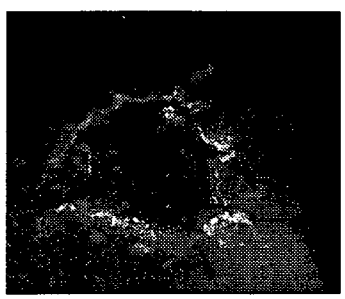
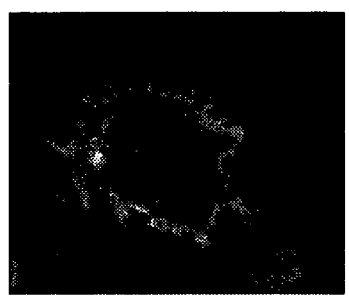
FIG. 5D
FIG. 5E
FIG. 5F
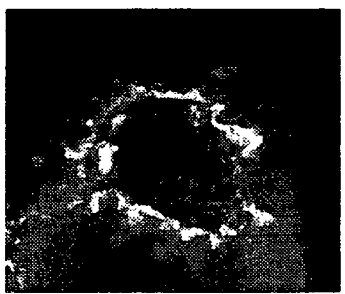
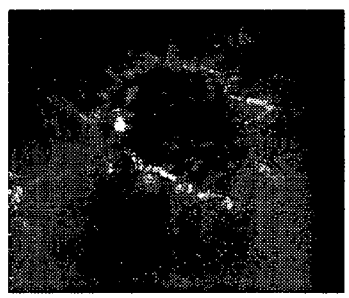
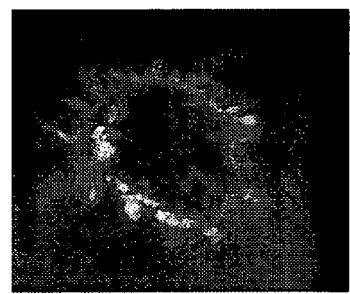
68 µm
FIG. 5G
70 µm
FIG. 5H
79 µm
FIG. 5I
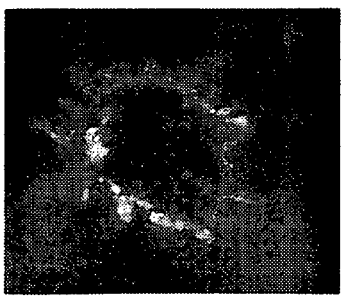
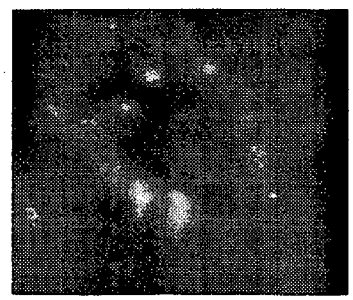
129 µm
FIG. 5J
170 µm
FIG. 5K 0 μm 17 μm 32 μm 48 μm 66 μm 71 μm 89 μm 130 μm 196 μm

MICROSCISSION PROCESSES AND PROCEDURES

CROSS-REFERENCE TO RELATED APPLICATIONS

This application is a continuation-in-part (CIP) of commonly owned U.S. application Ser. No. 09/878,155, filed 7 Jun. 2001, now U.S. Pat. No. 6,706,032. That application claimed domestic priority from U.S. Provisional Application Ser. No. 60/209,985, filed on 8 Jun. 2000. The teachings of these two applications are hereby incorporated herein by reference.

STATEMENT OF GOVERNMENT SUPPORT

This invention was made with government support under F19628-00-0002, awarded by the United States Air Force. The government has certain rights in the invention.

BACKGROUND OF THE INVENTION

Transdermal drug delivery, as the term is used generally, refers to permeation of the stratum corneum, the tough outer barrier of the skin, by a pharmaceutically active molecule. The stratum corneum, the thin (approximately 20 µm) outer layer of the epidermis, is dead tissue containing both multi-lamellar lipid barriers, and tough protein-based structures.

The epidermis, directly beneath the stratum corneum, also behaves as a lipid barrier. The dermis, directly beneath the epidermis, is permeable to many types of solutes. In the administration of a drug by topical application to skin, lipid-soluble drug molecules dissolve into and diffuse through the skin's multilamellar lipid bilayer membranes along a concentration gradient by virtue of the drug molecules' solubility in the lipid bilayer. Transdermal drug delivery may be targeted to a tissue directly beneath the skin or to capillaries for systemic distribution within the body by the circulation of blood.

The term "transdermal drug delivery" usually excludes hypodermic injection, long term needle placement for infusion pumps, and other needles which penetrate the skin's stratum corneum. Thus, transdermal drug delivery is generally regarded as minimally invasive. However, the low rate of transport of therapeutic molecules through the stratum corneum remains a common clinical problem.

Transdermal delivery of only a limited number of lipophilic drugs is commercially available. Existing methods include, for example, the use of wearable "patches," a passive transdermal drug delivery method that tends to be slow, and difficult to control.

Another method includes the use of a "gene gun," to accelerate 20 to 70 µm diameter drug particles, or smaller DNA-coated gold particles, to supersonic velocities, such that the particles pass through the stratum corneum into the epidermis or dermis. A single particle, 20 µm to 70 µm, in diameter, such as used in the gene gun, when fired at the stratum corneum at supersonic speeds, ruptures and tears through the tissues of the stratum corneum, epidermis and dermis, stopping and remaining at some depth which is determined by the initial velocity and mass of the particle. The resulting path through the above-mentioned tissues may be in the range of 1 µm to perhaps 30 µm because the tissues are elastic to various °s, depending on the individual. The semi-static analogue is to pierce a rubber sheet with a common pin, 750 µm in diameter. When pulled out of the rubber sheet, the resultant opening size is less than 1 µm, or perhaps not open at all. This is because the pin has torn the rubber sheet and pushed it aside, due to the rubber sheet's elasticity (ability to get out of the way), as the pin is forced through. As in the analogue, because of the elasticity of skin, use of the gene gun does not form microconduits in the skin because the tissue is only temporarily pushed aside as a particle is forced through the skin.

Examples of transdermal drug delivery methods presently being investigated include the use of ultrasound (sonophoresis) to cause cavitation in the stratum corneum; laser ablation of a small region of the stratum corneum, thereby providing access to the epidermis; the use of microneedles to create openings in the stratum corneum; the use of electrical methods, including low voltage iontophoresis, wherein transport is believed to occur through pre-existing aqueous pathways; and the use of high voltage pulses to cause electroporation of the skin. There are disadvantages associated with each of these methods. For example, often the rate of transport of molecules tends to diminish rapidly with increasing molecular size. Other disadvantages include pain and discomfort, skin irritation, the high cost and the large size of equipment required, and the potential for breaking off needles, which might remain imbedded in the skin.

Also, a common problem encountered in using established techniques such as subcutaneous and intradermal injection to deliver vaccines, is the inaccurate placement of the immunizing material with respect to the epidermal and dermal antigen-presenting cells, or with respect to keratinocytes. There is also a long-standing need for an effective method to deliver therapeutic agents to treat a fungal infection of the tissue underlying nail tissue of fingers and toes.

An existing problem with currently used methods of making biopotential measurements and other electrical measurements at the surface of the skin of a living organism is that the measurements are often degraded by motion and by other potentials that are associated with the skin. Techniques such as microscission or stripping of the stratum corneum of the skin can significantly improve the quality of such electrical measurements. However, mechanical alteration of the skin is highly undesirable, because it is difficult to control the ° of alteration; mechanical alteration can cause pain and discomfort, and can lead to infection. Therefore, there is a need for improved methods of making biopotential measurements at the surface of the skin.

The present invention satisfies these needs by providing, for example, an improved method of delivery of therapeutic agents to a tissue; an improved method of transdermal delivery of therapeutic agents; an improved method for delivering therapeutic agents to tissue underlying nail tissue; an improved method for obtaining samples of interstitial fluid or blood for sensing of analytes within the extracted fluid, including the measurement of analytes while within the microconduit; and an improved method of making biopotential measurements.

SUMMARY OF THE INVENTION

The present invention relates to methods and devices for forming microconduits in a tissue, and the uses of these microconduits in the modification and/or manipulation of body tissues. Thus, the present invention provides a method of modifying or manipulating body tissue by forming at least one microconduit therein, comprising the steps of:

a) accelerating a plurality of microparticles to a velocity that causes the microparticles to penetrate a region of a tissue surface upon impingement of the microparticles on the tissue surface;

b) directing the microparticles towards the region of tissue surface, thereby causing the microparticles to penetrate the tissue; and c) scissioning the tissue with the impinging microparticles, thereby forming a plurality of free microtissue particles, and thereby forming a microconduit;

wherein said microconduit is used for manipulation or modification of the body tissue in a manner selected from the group consisting of:

(1) extracting an analyte from the body tissue by removing the analyte from the tissue through the microconduit;

(2) forming a molecular matrix within at least one microconduit in body tissue by directing a molecular matrix into the microconduit;

(3) making at least one biopotential measurement across the body tissue by placing at least two electrodes in electrical connection with the body tissue with at least one electrode at the microconduit; and making a biopotential measurement across the electrodes;

(4) delivering at least one molecule to the body tissue by storing the molecule in at least one puncturable capsule in proximity to at least one microconduit;

(5) reducing pressure caused by a pool of blood beneath an injured or traumatized portion of body tissue by releasing the pressure through the microconduit;

(6) piercing the body tissue for a decorative purpose by inserting at least one wire through one or more microconduits;

(7) marking the body tissue with at least one identifying mark or at least one decorative mark by directing a dye or an ink into at least one microconduit;

(8) treating an infection below the surface of the body tissue by administering at least one therapeutic molecule or ion by directing the therapeutic molecule or ion into at least one microconduit, thereby delivering the therapeutic molecule or ion through the surface of the body tissue;

(9) removing hair from the surface of the body tissue by forming one or more microconduits at or near the hair follicles on the body tissue, followed by washing with water or aqueous solution, thereby removing the hair from the body tissue; and

(10) implanting hair into the surface of the body tissue by forming one or more microconduits having a diameter and depth sufficient to contain a new hair follicle on the body tissue, followed by implantation of a live hair follicle into the microconduits.

In preferred embodiments, the present invention, inter alia, includes the following, alone or in combination:

In one embodiment, a method for forming at least one microconduit in tissue includes the steps of: accelerating a plurality of microparticles to a velocity that causes the microparticles to penetrate a region of tissue surface upon impingement of the microparticles on the tissue surface; directing the microparticles towards the region of tissue surface, thereby causing the microparticles to penetrate the tissue; and scissioning the tissue with the impinging microparticles, thereby forming a plurality of free microtissue particles, and thereby forming a microconduit. As used herein, this procedure is referred to as the microscission process or microscissioning.

In another embodiment, a method for forming at least one opening in the stratum corneum of skin includes: accelerating a plurality of microparticles to a velocity that causes the microparticles to penetrate a region of the skin surface upon impingement of the microparticles on the skin surface; directing the microparticles towards the region of skin surface, thereby causing the microparticles to penetrate the skin; scissioning the skin with the impinging microparticles, thereby forming a plurality of free microtissue particles, and thereby forming a microconduit.

The invention also relates to a method of delivery of a therapeutic molecule or ion to tissue, the method including the steps of: accelerating a plurality of microparticles to a velocity that causes the microparticles to penetrate a region of tissue surface upon impingement of the microparticles on the tissue surface; directing the microparticles towards the region of tissue surface, thereby causing the microparticles to penetrate the tissue; scissioning the tissue with the impinging microparticles, thereby forming a plurality of free microtissue particles, and thereby forming a microconduit; and administering at least one therapeutic molecule or ion by directing the therapeutic molecule or ion into at least one microconduit, thereby delivering a therapeutic molecule or ion to tissue.

In another embodiment, a method of extracting an analyte from a tissue includes: accelerating a plurality of microparticles to a velocity that causes the microparticles to penetrate a region of a tissue surface upon impingement of the microparticles on the tissue surface; directing the microparticles towards the region of tissue surface, thereby causing the microparticles to penetrate the tissue; scissioning the tissue with the impinging microparticles, thereby forming a plurality of free microtissue particles, and thereby forming a microconduit; and removing the analyte from the tissue through the microconduit, thereby extracting the analyte from the tissue.

The invention also relates to a method for forming a molecular matrix within at least one microconduit, the method including the steps of: accelerating a plurality of microparticles to a velocity that causes the microparticles to penetrate a region of a tissue surface upon impingement of the microparticles on the tissue surface; directing the microparticles towards the region of tissue surface, thereby causing the microparticles to penetrate the tissue; scissioning the tissue with the impinging microparticles, thereby forming a plurality of free microtissue particles, and thereby forming a microconduit; and directing a molecular matrix into the microconduit, thereby forming a molecular matrix within the microconduit.

Another embodiment of the invention is a method of transdermal delivery of a therapeutic molecule or ion, the method including the steps of: accelerating a plurality of non-drug containing microparticles to a velocity that causes the microparticles to completely penetrate a region of a skin surface upon impingement of the microparticles on the skin surface; directing the microparticles towards the region of the skin surface, thereby causing the microparticles to penetrate the skin; scissioning the skin with the impinging microparticles, thereby forming a plurality of free microtissue particles, and thereby forming a microconduit; and administering at least one therapeutic molecule or ion by directing the therapeutic molecule or ion into at least one microconduit, thereby delivering the therapeutic molecule or ion through the stratum corneum and into the skin.

The invention also relates to a method for making one or more biopotential measurements across the skin, the method including the steps of accelerating a plurality of microparticles to a velocity that causes the microparticles to penetrate a region of a skin surface upon impingement of the microparticles on the skin surface; directing the microparticles towards the region of skin surface, thereby causing the microparticles to penetrate the skin; scissioning the skin with the impinging microparticles, thereby forming a plurality of free microtissue particles, and thereby forming a microconduit; placing at least two electrodes in electrical connection with the skin with at least one electrode at the microconduit; and making a biopotential measurement across the skin.

In one embodiment, the biopotential measurement is an electrocardiogram. In a particular embodiment, the electrocardiogram measurement is obtained during exercise stress testing. In yet another embodiment, the biopotential measurement is an electromyogram. The invention also relates to the use of microconduits made according to an embodiment for making biopotential measurements suitable for neuromuscular testing. In one embodiment, the biopotential measurement is an electroencephalogram to monitor anesthesia.

In a particular embodiment, a method of delivering at least one molecule to tissue includes the step of storing the molecule in at least one puncturable capsule in proximity to at least one microconduit. The stored molecule, according to an embodiment, may be included in a pharmaceutically acceptable carrier.

The invention also relates to a process for forming at least one microconduit through body tissue, particularly nail tissue, including the steps of: accelerating a plurality of microparticles to a velocity that causes the microparticles to penetrate a region of the nail tissue surface upon impingement of the microparticles on the nail tissue surface; and directing the microparticles towards the region of nail tissue surface, thereby causing the microparticles to penetrate the nail tissue surface; and scissioning the nail tissue with the impinging microparticles, thereby forming a plurality of free nail microtissue particles, and thereby forming a microconduit through the nail tissue.

Another embodiment of the invention includes a method for treating an infection of a body tissue, particularly tissue underlying nail tissue, including the steps of: accelerating a plurality of microparticles to a velocity that causes the microparticles to penetrate into the nail tissue surface upon impingement of the microparticles on the nail tissue surface; directing the microparticles towards the region of nail tissue surface; allowing the microparticles to impinge upon the region of nail tissue surface and to penetrate the nail tissue surface; scissioning the nail tissue with the impinging microparticles, thereby forming a plurality of free nail microtissue particles, and thereby forming a microconduit through the nail tissue; and then administering at least one therapeutic molecule or ion by directing the therapeutic molecule or ion into at least one microconduit, thereby delivering the therapeutic molecule or ion through the nail tissue.

Another embodiment of the invention includes a method for marking body tissue, particularly nail tissue, with at least one identifying mark or at least one decorative mark including the steps of: accelerating a plurality of microparticles to a velocity that causes the microparticles to partially penetrate into the nail tissue surface upon impingement of the microparticles on the nail tissue surface; directing the microparticles towards the region of nail tissue surface; allowing the microparticles to impinge upon the region of nail tissue surface and to partially penetrate the nail tissue surface; scissioning the nail tissue with the impinging microparticles, thereby forming a plurality of free nail microtissue particles, and thereby forming a microconduit through the nail tissue; and then directing a dye or an ink into at least one microconduit that partially penetrates the nail tissue, thereby marking the nail tissue.

Another embodiment of the invention includes a method for inserting at least one wire through at least one microconduit formed in body tissue, particularly nail tissue, including: accelerating a plurality of microparticles to a velocity that causes the microparticles to penetrate into a region of nail tissue surface upon impingement of the microparticles on the nail tissue surface; directing the microparticles towards the region of nail tissue surface, thereby causing the microparticles to penetrate the nail tissue surface; scissioning the nail tissue with the impinging microparticles, thereby forming a plurality of free nail microtissue particles, and thereby forming a microconduit through the nail tissue; and directing a wire into at least one microconduit, thereby inserting the wire through the microconduit.

In this embodiment, the microconduit is through the nail tissue where the nail has grown beyond the nail bed and extends out beyond all other tissue, as in a cantilever or overhang beyond the finger or toe. In one embodiment, an ornament or jewelry may be attached to the wire inserted in the microconduit.

The invention also relates to a method of reducing pressure caused by a pool of blood beneath an injured or traumatized section of body tissue, particularly nail tissue (e.g., a "blood blister") comprising the steps of: accelerating a plurality of microparticles to a velocity that causes the microparticles to penetrate a region of nail tissue surface upon impingement of the microparticles on the nail tissue surface; directing the microparticles towards the region of nail tissue surface, thereby causing the microparticles to penetrate the nail tissue surface; scissioning the nail tissue with the impinging microparticles, thereby forming a plurality of free nail microtissue particles, and thereby forming a microconduit through the nail tissue; and thereby releasing the pressure through the microconduit.

The invention also relates to a method of hair removal from body tissue, particularly skin tissue, comprising the steps of directing a flux of microparticles to a localized area that includes a hair, the microscissioning process will create a deep microconduit that includes the volume of the hair and hair follicle, thereby completely removing the hair of interest. Unlike electrolysis for hair removal the microscissioning process would be painless and will result in permanent removal of the hair. In other words, the hair won't grow back if the microconduit volume is coincident with the full hair structure. Washing the microconduit with water or an aqueous solution will remove essentially all microparticles, so that side effects associated with residual microparticles will be minimal to nonexistent.

The invention also relates to a method of hair implantation on body tissue, particularly scalp tissue, comprising the steps of directing a flux of microparticles to a localized area that will create a deep microconduit of a depth and diameter sufficient to accept a living hair follicle for implantation and continued growth. Unlike other methods of hair implantation (e.g., surgery) the microscissioning of scalp tissue for placement of live hair follicles will be painless and will provide a more dimensionally stable and well-controlled site for each hair implant. Washing the microconduit with water or an aqueous solution will remove essentially all microparticles, so that side effects associated with residual microparticles will be minimal to nonexistent.

The invention also relates to a mask for defining at least one localized area of a tissue surface region for formation of a microconduit by microparticle impingement. The mask includes a membrane that has a thickness in a range of between about one micrometer and about one thousand micrometers; at least one microhole in the membrane, the microhole having a diameter in a range of between about three micrometers and about one thousand micrometers. The embodiment further includes a means for positioning the membrane against the tissue surface, on the tissue surface, or near the tissue surface. In a particular embodiment, the mask is conformable to the tissue surface.

BRIEF DESCRIPTION OF THE DRAWINGS

FIGS. 5A-5K include confocal images at different depths, indicated in μm from the approximate surface of the skin, of a forearm microconduit formed according to an embodiment of the invention in Subject B.

DETAILED DESCRIPTION OF THE INVENTION

Figure 1:
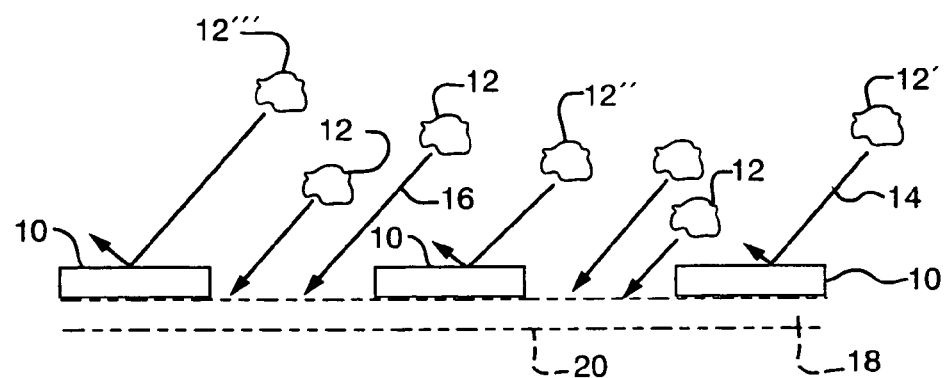
FIG. 1 is a schematic cross-sectional illustration of an embodiment of the invention of a method and an apparatus for making microconduits in tissue, wherein microparticles are viewed as impinging on a mask containing one or more microholes that expose localized regions of the skin surface.

The present invention relates to methods and devices for accelerating microparticles to a velocity that causes a plurality of microparticles to penetrate into a tissue surface upon impingement of the microparticles on the tissue surface; directing the microparticles towards an identified region of tissue surface; allowing the microparticles to impinge upon the region of tissue surface and to penetrate the tissue surface; scissioning the tissue with the impinging microparticles, thereby forming a plurality of free microtissue particles, and thereby forming a microconduit. As the term is used herein, "tissue" may include any collection of cells, for example, skin cells, including the stratum corneum and the epidermis; nail tissue, including toe nails and finger nails; and muscle cells.

As used herein, the term "microparticle" refers to a solid particle that has an approximate diameter or characteristic linear dimension in a range of between about 0.1 (one tenth) micrometer and about (three hundred) micrometers, or in a range of between about 1 (one) micrometer and about 100 (one hundred) micrometers. In one embodiment, the microparticle has a dimension of about 10 micrometers. In another embodiment, the microparticle has a dimension of about 100 micrometers. In yet another embodiment, microparticles having an average diameter of about 50 micrometers are used to produce a microconduit of a diameter sufficiently large to carry blood and chemicals.

As used herein, the term "microconduit" refers to a small opening, channel, or hole into, or through, a tissue, that allows transfer of materials by liquid flow, and by electrophoresis, the microconduit being formed upon impact of a plurality of microparticles on the surface of the tissue. In one embodiment, a microconduit may also allow materials to move through by diffusion or by convection.

The average size of a microconduit according to an embodiment is about one (1) mm or less in diameter. In one embodiment, a microconduit has a diameter in the range of between about 10 micrometers and about 200 micrometers. In another embodiment, a microconduit has a diameter in the range of about between 2 micrometers and about one (1) mm. In an embodiment of the invention, a microconduit is usually smaller than needles used for syringe injections, but has a characteristic size or diameter that is much larger than the diameters of carriers of analyte molecules, therapeutic molecules and ions, or the diameters of analyte molecules, therapeutic molecules and ions themselves. As used herein, the term "diameter" refers to the approximate diameter or characteristic linear dimension of at least one cross-section of an approximately cylindrical-shaped section of a microconduit. The term "diameter" is also used to refer to the approximate diameter or characteristic linear dimension of a microparticle or of a molecule.

The microconduit generating process includes using random shaped microparticles of a hard material for impingement on a tissue. In one embodiment, the major dimension of the particles is about 70 μm. In one embodiment, particles are accelerated to a velocity in the range of a meter/second, which is far less than a supersonic velocity (300 meters/sec). It is presently believed that when the particles strike the tissues of the skin, some of the particles stick to some tissue fragments and bounce off, carrying tissue fragments away; some particles heat some tissue to a temperature that disrupts the chemical bonds, and the molecules are reduced to their components of oxygen, hydrogen, nitrogen, and carbon mono or dioxide, which diffuse into the atmosphere, and yet other particles dislodge some tissue fragments by momentum transfer, 'knocking' them away from the locus of the microconduit. Thus, the microconduit formation may be a process that disassembles the skin components in tiny increments through various means and removes them by means of the gas or liquid flow that accelerates and carries the particles. The result is an open hole, reasonably circular in cross section throughout its total length. This has been clearly and repeatedly shown in the confocal microscope images taken of microconduits. See, for example, the images in FIG. 4A through FIG. 6I.

Locating a Tissue Surface Region

According to one embodiment of the invention, the first step in creating one or more microconduits into a tissue includes locating a suitable tissue surface region. In the case of a tissue exposed during surgery, the location would typically be determined by the skilled inspection of the tissue by the surgeon. For example, if microconduits were to be formed in cardiac tissue for purposes of introducing angiogenic molecules, the surgeon would locate the appropriate surface region of the heart. In another example, if a dermatological procedure, such as treatment of a skin lesion or condition is desired, the appropriate region of skin surface can be determined through its topography by a dermatologist. If transdermal drug delivery is desired, after being given general instruction, in many cases the patient can determine the particular region of skin surface (topographic region) to be used. In another example, if neonatal intensive care is desired, the attending physician or nurse would locate an appropriate cutaneous or skin surface region on an infant.

Acceleration of Microparticles

To form microconduits in tissue using microparticles, the microparticles are accelerated to a velocity such that their energy causes them to penetrate a region of tissue surface tissue upon impingement of the microparticles on the tissue surface.

According to one embodiment of the invention, microparticles are accelerated to a velocity that causes the microparticles to penetrate a tissue surface upon impingement of the microparticles on the tissue surface, and to scission or microscission the tissue, forming microconduits in tissue by using gas flow, in which the gas entrains the microparticles during the microparticle acceleration, thereby creating a flux of microparticles. As the microparticles approach the tissue surface, the gas can be preferentially expanded to obtain a significant velocity component parallel to the tissue surface, thereby minimizing gas entry into the microconduit. If the gas velocity perpendicular to the tissue surface is too large, gas can enter the tissue. The result, for deep microconduits, of gas entering the tissue, can be undesired delivery of gas deep into tissue. This problem is avoided by using gas flow that accelerates microparticles while the microparticles are distant from the tissue surface. If the microparticles are sufficiently massive, in terms of their volume and mass density, the microparticle momentum carries the microparticles into the tissue while the gas acquires enough parallel velocity that the gas does not enter the forming microconduits in significant amounts.

Gas flows suitable for use in an embodiment of the invention can be obtained in a number of ways. In one embodiment, by using over-pressure, in which the driving pressure for the gas flow is greater than one atmosphere absolute, the flowing gas can be used to accelerate the microparticles to a sufficient velocity to form microconduits on impingement on the tissue surface. For example, an over-pressured reservoir of gas such as a commercially supplied air cylinder can be used.

Alternatively, in some embodiments of the invention, a partial vacuum can be used to accelerate gas. A partial vacuum is sometimes referred to as a negative pressure, because it is a pressure less than that of one atmosphere absolute. A partial vacuum or suction creates the negative pressure. In an embodiment utilizing a partial vacuum to create gas flow, the risk of incidental delivery or injection of the flowing gas into the tissue in which one or more microconduits are being formed is reduced. In this case, the skin surface is exposed to less than one atmosphere. As a result, the possible injection of gas into the skin is less likely than it is when the gas flow is driven by a positive (greater than one atmosphere). To create a partial vacuum for use in an embodiment of the invention, the venturi effect can be used. According to an embodiment, to accelerate microparticles dispersed within a separate container, the container is kept at a pressure greater than the venturi pressure (usually atmospheric pressure). The gas flowing past an opening or orifice of the container then has a reduced relative pressure, and microparticles are thereby caused to move out of the separate container into the gas flow. This method is well known to those skilled in the art as the basis for relatively inexpensive microscission devices, such as an "air brush."

In one embodiment, because of its ready availability and low cost, either pressurized or ambient air, at about one atmosphere absolute, may be used as the microparticle-accelerating, flowing gas. The air should be either dry, dehydrated, or of low-moisture content. This is necessary because microparticles can clump together if their surfaces have water molecules on them. In one embodiment, nitrogen gas from a cylinder of compressed nitrogen or from a container of boiling liquid nitrogen is used. In one embodiment, an over-pressured reservoir such as a commercially supplied air cylinder can be used. In other embodiments, examples of gases suitable for use to accelerate microparticles include inert gases such as argon, either at normal atmospheric pressure, or at a higher or lower pressure than one atmospheric absolute.

A refrigerant gas, for example, 1,1,1,2 tetrafluoroethane, that significantly cools as it is expanded can also be used to accelerate microparticles. The temperature of 1,1,1,2 tetrafluoroethane drops to −60° F. when released from a spray can. This is important if microparticles, such as ice or solid water, which subsequently melt within the tissue, are used. In another embodiment, cooling of the tissue surface is used to alter mechanical and physical properties of the tissue before and/or during microparticle impingement. In one embodiment, cooling of the tissue surface occurs because the flowing gas used to accelerate the microparticles is at a temperature of below about 20° C.

In yet another embodiment, the microparticles are accelerated by means of a flowing liquid. In a particular embodiment, the flowing liquid is at a pressure greater than about one pound per square inch. In one embodiment, the temperature of the flowing liquid is below about 20° C.

According to another embodiment of the invention, microparticles are accelerated by impact with a moving solid surface that is moving at a sufficiently high velocity. One method for achieving a suitable moving solid surface is to use a rapidly rotating impeller. For example, in order to accelerate the microparticles, they can be drawn out of a container by means of evaporation or by reduced pressure, or pushed out by a positive pressure, and contacted with a rapidly rotating, hard surface.

Tissue Microscissioned or Compacted

According to an embodiment of the invention, microparticles are constrained to impinge mainly onto localized regions on the tissue surface, with such force that tissue material is removed by momentum transfer, "scissioned" or "microscissioned" from the tissue upon impact of the microparticles with the tissue. As used herein, the terms "scissioned," "microscissioned," "microscission," and grammatical variations thereof, refer to an opening up of the tissue, and the process of scission, microscission or opening up of tissue may involve removing part of the tissue by rendering tissue into gases or liquids, or by attachment of microparticles to parts of tissue and carrying them off by momentum transfer.

The process of scission or microscission of tissue, for example skin or nail tissue, according to an embodiment of the invention is a process of cutting, or microcutting, or cleaving the tissue, thereby forming a plurality of free microparticles of tissue, and thereby forming a microconduit. As the microparticles and air are forced into the tissue, the air turns around and carries out a majority of the newly formed microtissue particles and the impinging microparticles, thereby forming a microconduit in the tissue. The tissue is disassembled in a mechanical way by impinging microparticles.

In one embodiment, the tissue that is microscissioned is ejected from the tissue surface. Although a theoretical understanding of the interaction of impinging microparticles with tissue is not required to practice the invention, it is believed that the incident angle of the microparticle and the velocity may be important. During the initial stage of microconduit formation, when the forming microconduit depth is small, tissue material may be ejected from the forming microconduit. In the later stages of microconduit formation, when microconduit depth is greater, some cells of the tissue may be damaged, and the tissue may be progressively compacted, such that smaller amounts of tissue material are ejected from the microconduit than in the initial stages of microconduit formation. In another embodiment, microscission of tissue may relate to an opening up of tissue by compacting the tissue upon impingement of the microparticles on the tissue.

It is true that the deeper a microconduit is made, the more difficult it is for the incoming gas/particles to flow to the bottom of the dead end cylinder of the microconduit and for the spent particles and tissue particles to flow back upstream and exit the microconduit. Thus, the microconduit generation rate will diminish with depth and may possibly be used to predetermine the microconduit depth reached by controlling the diameter of the mask microhole and thus the diameter of the microconduit.

Microparticles Used

In one embodiment of the invention, solid, persistent microparticles that do not dissolve within the tissue after impinging, such as microparticles comprised of aluminum oxide, also referred to as "alumina," are used to form suitable microconduits.

Another class of microparticles suitable for use in an embodiment include solid phase microparticles comprised of biocompatible substances that exist in the liquid state at normal physiologic tissue temperatures, for example normal human body temperature, which is about 37° C., in the interior, and often lower at the skin's surface. In one embodiment, the microparticles have a melting point less than about 33° C. Such solid phase microparticles impinge onto a localized region of tissue surface, and enter into the tissue, creating microconduits. Such solid phase microparticles melt within the tissue, and the resulting liquid mixes with tissue interstitial fluid. The change to the liquid state further results in diffusion and removal of the microparticle material. Accordingly, in one embodiment, microparticles comprised of solid water (water ice) or other tissue soluble material are used. In another embodiment, use of microparticles that are water soluble and dissolve within a tissue after impingement also has the advantage that the particles do not persist within the tissue. It is important, however, to use microparticle materials that do not cause significant localized irritation or localized tissue damage while dissolving. This can be accomplished by choosing microparticle materials that have an acceptable combination of lack of irritation and rapid diffusion of soluble molecules away from the site of the microparticle in the tissue.

In one embodiment, microparticles comprised of soluble, biocompatible substances may be used to form microconduits. In a particular embodiment, microparticles may include sodium bicarbonate, which readily dissolves in water within a tissue, particularly the epidermis. Sodium bicarbonate occurs naturally in the body, and is essentially nontoxic. Temporarily elevated concentrations of bicarbonate can cause temporary local pH increases, but these are not believed to cause significant side effects. If such a pH increase is undesirable, in one embodiment microparticles comprised of a buffering mixture of sodium acetate and sodium bicarbonate can be used. Upon dissolution of such buffered microparticles, only an insignificant pH change from the normal epidermal pH will occur. In yet other embodiments, microparticles are comprised of other nontoxic, suitable salts such as lactates, sterates, and the like. Urea is another naturally occurring substance that is relatively nontoxic. Accordingly, in another embodiment, microparticles are comprised of urea or urea salts.

In another embodiment, microparticles include solid phase microparticles comprised of biocompatible substances that exist in the gaseous state at normal physiologic tissue temperatures. In a particular embodiment microparticles are comprised of solid phase carbon dioxide, also known as "dry ice." As is well known through use of carbon dioxide in fire extinguishers, solid carbon dioxide can be formed by rapid expansion from the liquid phase. After impingement and entry into tissue, solid carbon dioxide microparticles of appropriate size sublime rapidly within the tissue and thereby cause a pressure burst. The impinging solid carbon dioxide microparticles first contribute to microconduit formation, then undergo an almost explosive burst that also contributes to formation of the microconduit, as gaseous carbon dioxide rapidly forms. The pressure of the expanding gas assists microconduit formation because the rapid sublimation of impinging carbon dioxide microparticles causes an almost explosive release of gas within the forming microconduit. However, if solid carbon dioxide is used, care must be taken if a significant number of carbon dioxide microparticles remain in the tissue, because a several order of magnitude increase in volume occurs as the solid carbon dioxide sublimes to form gaseous carbon dioxide.

In one embodiment, solid phase microparticles contain solutes, including one or more therapeutically effective substances or drugs, and serve to deliver drugs into the skin upon subsequently melting. As used herein, the terms "therapeutically effective substance" or "therapeutic substance" or "drug" include:

(i) Compounds and compositions recognized in the official United States Pharmacopoeia, the official Homeopathic Pharmacopoeia of the United States, or the official National Formulary, or any supplement of any of them;

(ii) Compounds and compositions intended for use in the diagnosis, cure, mitigation, treatment, or prevention of disease in man or other animals; and (iii) Compounds and compositions (other than food) intended to affect the structure or any function of the body of man or other animals.

In another embodiment, inert microparticles, such as ceramic carriers or polymeric carriers, may be used to both form microconduits and to serve as slow-release devices.

An Apparatus for Impinging Microparticles

This invention also relates to an apparatus for use in creating one or more microconduits by microparticle impingement. In one embodiment, the apparatus includes a means for accelerating a plurality of microparticles to a velocity that causes the microparticles to penetrate into a surface of the tissue upon impingement of the microparticles on the tissue surface; a means for directing the microparticles towards a region of tissue surface; and a means for allowing the microparticles to impinge upon the region of tissue surface and to penetrate the tissue surface, thereby forming a microconduit in the tissue. Thus, the apparatus can create a flux of microparticles that is concentrated, and that impinges on one or more small, localized regions of a tissue.

Controlling the Amount of Microparticles and Controlling the Region of Tissue Surface Impinged by Microparticles In one embodiment, the amount of microparticles that are allowed to impinge upon a region of tissue surface is controlled by controlling the area of the region of tissue surface exposed to incoming, accelerated microparticles.

According to an embodiment of the invention, localized areas of tissue surface can be defined by use of a mask comprising a membrane placed on, at, or near the tissue surface, the mask containing one or more microholes. In this embodiment, microparticles directed towards the mask impinge onto a localized area of a tissue surface region if they pass through a microhole in the mask. In one embodiment, the microholes have a diameter in a range of about three micrometers and about one thousand micrometers. According to an embodiment, a suitable mask can be fabricated from a membrane (a thin sheet of material that typically has an area of several square millimeters or more). The mask prevents microparticles from passing through the mask material. As used herein, the term "membrane" refers to a small sheet of material that is much larger in lateral extent than the localized areas onto which microparticle impingement is sought. According to an embodiment, the membrane has at least one microhole that defines the local tissue surface area when the mask is held against, or next to, a tissue surface. Much of the tissue surface is thereby protected from microparticle impingement, such that localized surface areas are defined by the restriction that microparticles can only reach the tissue if the microparticles are incident within a microhole. In an embodiment in which a mask is used in forming a microconduit, generally the microconduit opening at the tissue surface is smaller than the microhole. In one embodiment, the membrane may be conformable to the tissue surface.

According to an embodiment, suitable masks may be formed from sheets made of solid materials such as metals, metal alloys, polymers, silicon, passivated silicon, ceramics and glasses. In a particular embodiment, a mask may be comprised of a solid biocompatible material such as titanium, stainless steel, polyimide, nylon, poly (lactic-co-glycolic acid), calcium aluminum phosphate, and the like. Depending on the method used to accelerate the microparticles, masks of a variety of thicknesses may be suitable for use in an embodiment. In one embodiment, a mask has a thickness in the range of about one (1) micrometer to about one thousand (1,000) micrometers (µm). In the case of gas-accelerated microparticles, it is presently preferred to use masks with a thickness of about twenty five (25) to about one hundred (100) µm. In one embodiment, a mask has a thickness of about 50 µm. In another embodiment, a mask has a thickness of about 75 to about 100 µm. A mask as thin as perhaps one micrometer could be used if it didn't wear away by the impinging particles before the desired microconduit was generated. Also, a 1 micrometer membrane, even if it continued to mask for the 4 to 14 seconds required to form a microconduit, would likely not have the stiffness to stay tightly against the stratum corneum. Masks with multiple microholes tend to 'billow up' away from the stratum corneum, and must be stiff enough to completely resist this gas-driven 'sail' phenomenon. As is well known to those skilled in the art of semiconductor microfabrication, a variety of established techniques can be used to form microholes in a mask. Suitable techniques include use of rotating drills, use of laser energy, and spatially constrained chemical, plasma, or reactive ion, or ion etching.

According to an embodiment, the fabricated mask can be held against a tissue by a variety of methods. In the case of transdermal microconduit formation, one embodiment comprises holding a mask mounted on a holding fixture which also holds and aligns the gas/particle emitting nozzle against the skin, such as the forearm, by using an elastic strap, similar to a snugly fitting wrist watch. In a particular embodiment of the invention, formation of microconduits through the stratum corneum typically requires 4 to 20 seconds of microparticle impingement. A short time is used to put on the mask/strap, so that the total time of holding the mask firmly against the skin is at most a few minutes.

FIG. 1 is a schematic, cross-sectional illustration of one embodiment of the invention of a method and an apparatus for making microconduits in tissue. In this embodiment, the tissue comprises the stratum corneum 18. In FIG. 1, microparticles are viewed as impinging on a mask 10 disposed on the stratum corneum 18 of skin. Mask 10 defines one or more microholes that expose localized regions of the skin surface. The plurality of irregular-shaped objects (12, 12", 12, 12''') from which arrows 14, 16 emanate represent impinging microparticles. The mask or micromask material 10 blocks microparticles 12' through 12" from reaching the surface of the tissue. The microparticles 12' through 12''' bounce off the mask material in a direction shown generally by arrow 14, without reaching the stratum corneum 18, or the epidermis 20. The microparticles 12 traveling in a direction shown generally by arrow 16 pass through the microholes in the mask and impinge upon the surface of the stratum corneum 18. It should be noted that in a preferred embodiment the angle at which microparticles impinge upon a tissue, including the stratum corneum, is close to ninety (90) degrees. The angle of impingement may be controlled, in different embodiments, by collimating the microparticles, as described below.

In order to define one or more localized areas for microparticle impingement, one or more microholes with microhole size (diameter if essentially circular) in a range of between about three micrometers (3 µm) and to about one thousand micrometers (1000 µm) are provided in the membrane. The mask is held snugly against the tissue surface region. Incident microparticles are thereby constrained to impinge only onto the localized tissue areas exposed through the microholes in the mask. According to an embodiment of the invention, it is necessary that the microholes be somewhat larger than the microparticles, and therefore, the opening of the microconduit formed in tissue is generally smaller than the microholes in the mask.

Any of several attachment or positioning means are satisfactory for temporarily holding the mask against a tissue surface region. In one embodiment, an adhesive backing can be provided on the side of the mask that is to contact the tissue surface region. Pressure contact can also be used, for example, by affixing a strap that goes around the body or body part such that the mask is held against the tissue. For example, if the tissue surface region is the skin of the forearm, a strap similar to that used on a wrist watch can be used. In one embodiment, a mask may also be incorporated into a device that contains the source of microparticles, such that placing the device against a tissue allows microparticles to be impinged onto localized areas in order to make one or more microconduits.

According to another embodiment, a region of tissue surface is defined by directing a collimated beam of microparticles onto the region of tissue. In a particular embodiment, the size (for example, the diameter, if a cross-section of a circular beam is used) of the microparticle beam is the main determinant of the diameter of the resulting microconduits.

The idea of collimating the particle stream is that, in a perfectly collimated column, all particles would be moving parallel to one another and perpendicular to the surface upon which they impinged, assuming that the stream itself was perpendicular to the surface. Thus, the diameter of the surface upon which the particles impinged would be the same as the diameter of the particle stream. Normally, the components of a particle-loaded gas stream would diverge, growing larger in diameter the greater the distance from the particle source. A perfectly collimated particle stream would not diverge, and if the stream diameter could be 150 µm, no mask would be needed, the microconduit would be 150 µm in diameter also. Perfect collimation is impossible to achieve, so a mask, using a well collimated stream, is required to more precisely define the microconduit diameter at the surface of the stratum corneum. However, if the mask is not tight against the stratum corneum, the stream will begin diverging as it leaves the underside of the mask. With rather good collimation, this effect is small, and every microhole in the mask does not need to be tight against the stratum corneum, because even though it isn't the beam size, it is close to the mask microhole diameter.

Figure 2:
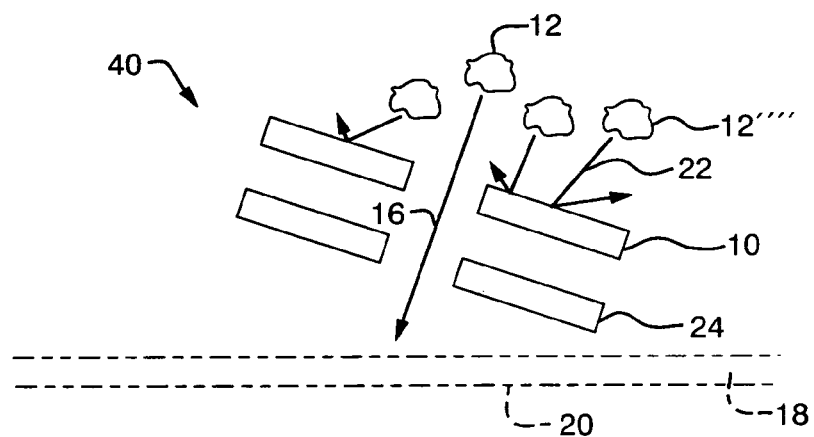
FIG. 2 is a schematic cross-sectional drawing of a collimated beam of microparticles according to one embodiment of the invention impinging onto a region of skin surface.

One way to collimate the stream is to use a nozzle with a long bore of the desired diameter. FIG. 2 shows another way, where only the ends of a long bore exist. In FIG. 2, a plurality of masks, generally indicated by 40, includes mask 10 and mask 24. An incoming, slightly divergent particle stream hits the top of the mask 10, which filters out the most divergent particles. The better collimated particles then go through the microholes in that mask, and diverge only slightly before reaching the lower mask 24, which filters out those particles that diverge too much. The particles exiting mask 24 are well enough collimated that mask 24 does not need to be held tightly against the stratum corneum, 18 in order to produce microconduits nearly the same size as the microholes in mask 24.

In FIG. 2, at least two sheets of material (10, 24) are positioned so as to substantially prevent microparticles (12"") from reaching some areas of the tissue, with the result that microparticles 12"" strike the mask and bounce off in the direction shown by arrow 22, for example.

Impinging microparticles (12), traveling in the direction shown by arrow 16, predominantly strike one or more localized areas of the tissue surface. FIG. 2 shows that the use of at least two sheets of mask material can serve to approximately collimate the impinging microparticles according to an embodiment of the invention.

In one embodiment, the amount of microparticles that are allowed to impinge upon a region of tissue surface is controlled by controlling the amount of time that microparticles are allowed to impinge on the region of tissue. This is true whether or not a collimated microparticle beam is used. In one embodiment, the time of microparticle impingement onto tissue surface, and the amount of microparticles impinging on a region of tissue surface can be controlled by scanning the beam over the region of tissue surface, and by using both the scan rate (velocity across or parallel to the tissue surface) and the time the beam is on or off. According to an embodiment, the on/off time can be controlled by gating the beam, for example, by moving a deflecting solid surface out of or into the beam.

In one embodiment, control of the microparticle amount can be accomplished by an indirect method in which the microparticle beam is calibrated in separate measurements, such that timing of the "ON" time thereafter controls the amount of microparticles impinging onto a localized surface area. Here, a test material in which a microconduit can be easily measured is subjected to the particle beam for a fixed amount of time. The resulting 'test' microconduit depth is measured microscopically. By having performed calibration experiments relating the microconduit depth in the test material to the microconduit depth in a human subject's skin, an exposure time can be elucidated to generate the desired microconduit depth in the human subject.

The number of microparticles per unit volume in a gas stream of a given diameter and velocity can be varied. This can be done by metering the particles from the particular reservoir into the gas stream through: a) changing the aperture diameter and/or the number of apertures through which the particles fall from the particle reservoir into the passing gas stream, or b) changing the rate and/or amplitude at which the particle reservoir is shaken to dislodge the particles and bring them across the aperture to fall into the gas flow.

In a particular embodiment, a particle flux which is generally used to produce a microconduit is about one million particles per second. Based on a calibrated count and weight of particles, the number of particles per second transmitted in a flux can be determined through the time/weight relationship.

The same is true with the delivery of particles by the 'impeller' approach. The number of particles per unit time being hit by the impeller can be varied by the number of particles available to be hit.

Generally, by impinging microparticles onto a localized area equal to a range of about between about 100 square micrometers and about one million square micrometers (for example, an area with a diameter of about five to about one thousand micrometers (5-1000 μm)), microconduits with approximately the same cross-sectional size can be formed. In one embodiment, the microparticles impinge upon the region of tissue surface which has an area in a range of between about 100 square micrometers and about two million square micrometers.

In the case of skin, according to one embodiment, microparticles are impinged onto a localized area equal to between about 1000 square micrometers and about 100,000 square micrometers (for example, an area with a diameter of about 30 to about 300 micrometers), to form microconduits of approximately the same cross-sectional size.

The present invention also relates to an apparatus suitable for formation of microconduits in tissue by microparticle impingement. In one embodiment, an apparatus includes a scannable microparticle beam collimator with an on/off gating means; a source of moving microparticles; at least one solid surface with at least one beam-defining aperture; a means for gating the microparticle beam between "ON" and "OFF;" a first excess particle collection duct and suction means, for recovering microparticles that do not pass through the beam-defining aperture; and a second excess particle collection duct and suction means, for recovering microparticles that pass through the beam-defining aperture, impinge onto the tissue, and rebound from the tissue. In one embodiment the beam-defining aperture of the apparatus is, for example, in the size (diameter) range of about between five micrometers (5 μm) and about two thousand micrometers (2000 μm); in another embodiment the aperture size is in the range of between about thirty micrometers (30 μm) and about one thousand micrometers (1000 μm). In another embodiment, the apparatus can comprise more than two solid sheets provided with at least one collimating aperture, to further collimate the microparticle beam.

According to an embodiment, the depth of the microconduits formed by microparticle impingement can be regulated by controlling the amount (number or total mass) of the impinging microparticles, the size (individual mass) of impinging microparticles, the speed (magnitude of the microparticle velocity), the angle of impingement (direction of the microparticle velocity) the hardness of the microparticles, the shape of the microparticles, the sharpness (cutting ability) of the microparticles, the total number or amount of impinging microparticles that impact a local surface area, the mask geometry (microhole size and mask thickness), and in some cases, the mask material (which can govern the ° of elasticity and the amount of scattering of microparticles from the walls of the microholes of the mask). The viscosity and velocity of any gas between the microparticle source and the local area onto which microparticles impinge can also affect microconduit formation.

Humidity Depth Sensors

According to an embodiment, the formation of microconduits and the depth of the microconduits formed by microparticle impingement can be guided in whole, or in part, by sensing or measuring the humidity of the gas that is returned from the forming microconduit. For example, the stratum corneum and the nail plate of finger and toe nails have a low water content compared to viable underlying tissue. A dry gas can be used to accelerate and impinge the microparticles on a microlocalized area of the skin or nail. Gas that enters and then returns from a microconduit can acquire water according to the wetness of the tissue into which the microconduit penetrates. A microconduit that does not penetrate the stratum corneum (or nail) will transfer less water to the gas.

The gas flow can be essentially continuous, or if it is desired, the gas flow can be stopped or interrupted (modulated) to increase its water content. Some of the gas which flows away from the microconduit site can be monitored for humidity, using humidity sensors, such as electrical capacitance-based humidity sensors. Examples of the general principle of such humidity sensing can be found in Schiffinan et al., "Airway humidification in mechanically ventilated neonates and infants: a comparative study of a heat and moisture exchanger vs. a heated humidifier using a new fast-response capacitive humidity sensor," *Crit. Care Med.* 25:1755-1760 (1997); and Ohhashi et al., "Human perspiration measurement," *Physiol. Meas.* 19: 449-461 (1998), the teachings of which are incorporated herein by reference in their entireties.

Modification of Tissue Surfaces

According to an embodiment, the general process of the invention can also be carried out by including the additional step of applying one or more conditions at the surface of the tissue in order to alter the mechanical properties of the outer layer of the tissue surface. For example, in one embodiment, the interaction of impinging microparticles with the outer layer can in some cases be varied by changing the hardness of the outer layer. In particular, it may be noted that impinging microparticles tend to scission a harder surface, and then bounce off after impingement, also removing parts of the harder surface. In contrast, if microparticles impinge onto a softer surface, microparticles tend to penetrate into, and then reside, within the tissue. Accordingly, because many tissues become more rigid as the temperature is decreased, in one embodiment, cooling may be used to increase the hardness of a tissue surface layer. Thus, applying a cooling stream of gas or liquid to the tissue before microparticle impingement can be used in an embodiment to harden the tissue surface. In the case of skin, cooling of the skin's surface before impingement by microparticles may decrease sensation.

In the case of the skin, the outer region of the nonviable stratum corneum layer is often significantly harder than the viable epidermis. If, however, the skin's surface is placed in contact with water, or is occluded such that exiting water accumulates within the stratum corneum, the stratum corneum becomes softer. Accordingly, one embodiment includes the step of applying a desiccating material that hardens the stratum corneum by removing water. Suitable materials for use in an embodiment include isopropyl alcohol, ethanol, and other alcohols. In a particular embodiment, drying the stratum corneum partially by a dry gas stream, such as dry air, can also be used.

According to an embodiment, after a microconduit is formed, recovery processes begin that eventually lead to full restoration of the skin's barrier function. As the term is used herein, "recovery" of a microconduit refers to the self-repair process in which the tissue that has been microscissioned away is replaced by newly grown tissue. One common feature of recovery is the re-establishment of lipid membranes, which allow passage of nonpolar molecules, but exclude ions and charged molecules. In the human skin approximately one hundred (100) lipid bilayers must be penetrated to pass completely through the stratum corneum. In one embodiment, following formation of a microconduit, the permeability of the skin at the site of the microconduit can be increased by applying one or more electrical pulses. The electrical pulses applied cause electroporation of at least one lipid-containing membrane. In a particular embodiment, the newly formed microconduit is allowed to recover for a period of time before the electrical pulse is applied. As used herein, the term "partially recovered" as it applies to a microconduit, means that the tissue, removed or damaged by impinging microparticles that formed the microconduit, has begun to repair itself or to grow new tissue. Although fifty (50) to three hundred (300) volts typically are needed to achieve electroporation of human skin that has not been subject to a process for formation of one or more microconduits, the voltage of an electrical pulse can be less than 50 volts to achieve microlocalized electroporation of skin that has already undergone microconduit formation, and undergone partial recovery.

A partially recovered microconduit is a site that preferentially experiences electroporation, because a voltage across the stratum corneum associated with either an electrical current pulse ("current clamp" pulse) or an electrical voltage pulse ("voltage clamp" pulse) will concentrate mostly across fewer lipid membranes at the site of a partially recovered microconduit. For example, if approximately five (5) lipid bilayer membranes have been formed within or near the epidermal entrance to a stratum corneum-penetrating microconduit, then a pulse needs to cause only approximately five (5) V across the partially recovered microconduit. This is much less than the fifty (50) to three hundred (300) V associated with localized transport regions (LTRs) caused by electroporation in human skin not subjected to microconduit formation processes. For a description of such localized transport regions see, for example, Pliquett, et al "Imaging of Fluorescent Molecules and Small Ion Transport Through Human Stratum Corneum During High-voltage Pulsing: Localized Transport Regions are Involved," 58 J. Biophys. Chem.,185-204, 1996; Prausnitz et al. "Imaging Regions of Transport Across Human Stratum Corneum During High Voltage and Low Voltage Exposures," 85 J. Pharm. Sci. 1363-1370, 1996; Weaver, et al. "Theory of electrical formation of aqueous pathways across skin transport barriers," 35 *Advanced Drug Delivery Reviews* 21-39, 1999; and Gowrishankar et al., "Spatially Constrained Localized Transport Regions Due to Skin Electroporation," 60 *J Controlled Release,* 101-110, 1999, the teachings of which are incorporated herein by reference in their entireties. Although the processes governing formation of LTRs in human skin subject only to electrical pulses are not fully understood, preferential electroporation at skin sites with lipid membranes is qualitatively consistent with LTR formation.

In another embodiment, microscopic aqueous pathways associated with electroporation of lipid membranes at the site of a partially recovered microconduit are altered by the further step of applying at least one modifying agent. The modifying agent serves to alter aqueous pathways formed by electroporation, and can be used to additionally assist the re-opening of a microconduit that has been partially closed off by natural recovery processes. This embodiment includes the application of long, linear molecules that enter aqueous pathways formed by electroporation of lipid-containing membranes, such as cell membranes, or one or more multilamellar lipid bilayer membranes of a recovering stratum corneum. Suitable modifying agents for use in an embodiment include dextran, heparin, and DNA. Such modifying agents can prolong the lifetime of aqueous pathways through lipid membranes, and can also alter the size of the aqueous pathways through lipid membranes. This increases the permeability of a partially recovered microconduit and also decreases the electrical resistance of a partially recovered microconduit.

The invention also relates to a method for altering, and thereby controlling, the recovery response to formation of one or more microconduits. As used herein, the term "recovery" refers to the re-growth of tissue removed or otherwise damaged by the formation of microconduits, as to close off and seal the opening of a microconduit at the tissue surface. An embodiment of the method includes supplying (or removing) chemical agents at the site of the entrance to one or more microconduits, or at a site within microconduits, such that the concentration of the chemical agents is controlled. Controlling the concentration of chemical agents within the tissue surrounding a microconduit can alter the rate of recovery of the tissue and of the microconduit. Although eventual recovery is generally sought, it can be advantageous to either cause delay in the recovery (keeping the microconduit open), or to accelerate recovery, once desired molecular and ionic transport or measurements have been accomplished.

This method is particularly useful with transdermal microconduits. In one embodiment, calcium ion ($Ca^{2+}$), for example, is used as the chemical agent. If $Ca^{2+}$ is present at relatively high concentrations within the microconduit, then the $Ca^{2+}$ concentration within the epidermis is also high, and repair and recovery processes tend to be inhibited, and the microconduits tend to remain open and available for molecular and ionic transport. In another embodiment, 5-fluorouracil is used to delay or prevent recovery of a microconduit.

In yet another embodiment, a retinoid such as retinoic acid; a surfactant; or an antigen is used to delay recovery of a microconduit. In a particular embodiment, the chemical agent used to delay repair and recovery of the microconduit is topically applied to the opening of the microconduit, directed into the opening, and applied to tissue surrounding the opening. In a particular embodiment, the chemical agent directed into the opening is in a column, for example, a pipet or capillary tube, and the column is sealed to the tissue around the microconduit. Next, pressure is directly applied to the microconduit, for example, by squeezing a rubber bulb attached to one end of the column or pipet, thereby forcing the chemical agent included in the column or pipet into the microconduit. The chemical agent is absorbed by the tissue surrounding the microconduit.

The method for altering, and thereby controlling, the skin's recovery response to formation of one or more microconduits by controlling the concentration of chemical agents within the tissue surrounding a microconduit is applicable also to microconduits formed by electroporation and keratolytic agents (see, for example, U.S. Pat. No. 5,911,223 to Weaver et al., "Introduction of Modifying Agents into Skin by Electroporation," Jun. 15, 1999; Zewert et al., "Creation of Transdermal Pathways for Macromolecule Transport by Skin Electroporation and a Low Toxicity, Pathway-Enlarging Molecule," *Bioelectrochem. Bioenerget.* 49:11-20, 1999; Ilic et al., "Spatially Constrained Skin Electroporation with Sodium Thiosulfate and Urea Creates Transdermal Microconduits," 61 *J. Controlled Release,* 185-202, 1999), the teachings of which are incorporated herein by reference in their entireties.

The method for controlling the skin's recovery response to formation of one or more microconduits by controlling the concentration of chemical agents within the tissue surrounding a microconduit is applicable also to micropores in skin formed by localized laser ablation (see, for example, S. L. Jacques et al., "Controlled Removal of Human Stratum Corneum by a Pulsed Laser," 88 *J Invest. Dermatol,* 88-93, 1987; by ultrasound (see, for example, N. Yamashita et al., "Scanning Electron Microscopic Evaluation of the Skin Surface After Ultrasound Exposure," 247 *The Anatomical Record* 455-461, 1997; T. Hikima et al., "Effect of Ultrasound Application on Skin Metabolism of Prednisolone 21-Acetate," 15 *Pharm. Res.,* 1680-1683, 1998; J. Wu et al. "Defects Generated in Human Stratum Corneum Specimens by Ultrasound," *Ultrasound in Med. & Biol.* 24:705-710, 1998)), the teachings of which are incorporated herein by reference in their entireties. This method of altering the recovery of skin is also applicable to microconduits or skin openings formed by "thermal poration" (see, for example, U.S. Pat. No. 6,142,939 to J. A. Eppstein et al., "Microporation of Human Skin for Drug Delivery and Monitoring Applications;" A. Smith et al., "Fluorescein Kinetics in Interstitial Fluid Harvesting from Diabetic Skin during Fluorescein Angiography: Implications for Glucose Monitoring," 1 *Diabetes Tech. Therapeut.* 21-27, 1999); by insertion and removal of microneedles (see, for example, S. Henry et al. "Microfabricated Microneedles: A Novel Approach to Transdermal Drug Delivery," 87 *J. Pharm. Sci.* 922-925, 1998); or by any other means for creating a stratum corneum-penetrating opening less than about five hundred micrometer (500 µm) in diameter or characteristic length within the opening. The teachings of the above cited publications are incorporated herein by reference in their entireties.

Examples of methods and apparatus used in electroporation; in controlling transport of molecules across tissue using electroporation; in treatment of cells in a tissue; and in making biopotential measurements, include those which are disclosed in related U.S. Pat. No. 5,019,034 to Weaver et al.; U.S. Pat. No. 5,019,034 to Weaver et al.; U.S. Pat. No. 5,389,069 to Weaver; U.S. Pat. No. 5,547,467 to Prausnitz et al.; U.S. Pat. No. 5,667,491 to Pliquett et al.; U.S. Pat. No. 5,749,847 to Zewert et al.; U.S. Pat. No. 5,983,131 to Weaver et al.; U.S. Pat. No. 5,911,223 to Weaver et al.; U.S. Pat. No. 6,085,115 to Weaver et al; and in related U.S. application Ser. No. 60/189,670, filed on Mar. 15, 2000; Ser. No. 60/209,985, filed on Jun. 8, 2000; and Ser. No. 60/228,488, filed on Aug. 28, 2000. The entire teachings of the above-referenced patents and applications are incorporated herein by reference in their entireties.

Other Embodiments

Other embodiments of the invention relate to microconduits that penetrate partially or fully through the skin's stratum corneum, the microconduits formed by microparticle impingement onto one or more localized surface areas of the stratum corneum. According to an embodiment, microconduits that fully penetrate the stratum corneum are of particular interest, because such microconduits provide large aqueous pathways for molecular and ionic transport through the stratum corneum, the skin's main barrier to ionic and molecular transport. Because microconduit size, according to an embodiment, is much larger than even macromolecules such as proteins and nucleic acids, transport occurs with insignificant steric hindrance. For this reason, trans-stratum corneum microconduits or trans-corneal microconduits can provide transdermal transport of essentially any size molecule.

According to an embodiment, suitable transdermal microconduits that fully penetrate the skin's stratum corneum can be formed by using microparticles which do not dissolve within the tissue after impinging. In such an embodiment, it is preferred to form microconduits which do not exceed a range of between approximately forty micrometers (40 µm) and sixty micrometers (60 µm) in depth, as measured from the outer surface of the stratum corneum. At this depth the microparticles remain within the viable epidermis, and above the stratum basal epidermidis (a layer of stem cells that continually replenishes the epidermis and stratum corneum). As a result, in approximately two weeks the entire epidermis is replaced and renewed, with epidermal cells differentiating and moving outward to replenish the nonviable stratum corneum, and carrying the water insoluble microparticles out of the body. According to an embodiment, although water insoluble microparticles within this depth in the epidermis do not dissolve in the epidermal tissue, the microparticles usually do not remain in the tissue for more than approximately two weeks. Microparticle materials which do not cause irritation are therefore suitable for creating transdermal microconduits which do not exceed approximately forty to sixty micrometers (40-60 µm) in depth.

A present preferred embodiment is to form microconduits less than about fifty micrometers (50 µm) in depth by using aluminum oxide (alumina) microparticles that are irregular in size, and that have a characteristic linear dimension of about thirty to seventy micrometers (30 to 70 µm).

According to an embodiment, microconduits deeper than fifty micrometers (50 µm) can also be formed if the microparticle material is sufficiently inert. Presently it is preferred to use microparticles comprised of aluminum oxide (alumina) to form microconduits deeper than approximately fifty micrometers (50 µm). In some cases, however, a granuloma can be formed by cells which phacytose such microparticles. Such granulomas may occur when microparticles penetrate the entire epidermis and become lodged in the underlying dermis.

This invention also relates to a method of detecting the appearance of blood within one or more microconduits, before blood entering a microconduit moves out of the microconduit and then leaves the tissue in which the microconduit(s) is formed. According to an embodiment, detection of blood within one or more micro conduits can be used to assess the size, particularly depth, of a microconduit if the tissue is known to have blood vessels such as a capillary bed located away from the tissue surface where microconduits are formed.

According to a preferred embodiment, a method for detection of blood within one or more microconduits includes the use of optical means that employs reflected light which has spectral properties different than reflected light from the tissue in which the microconduit is formed. For example, measurement of the ratio of reflected red light to reflected blue light can give an indication of the entry of blood into a microconduit.

According to an embodiment, for detection of blood within one or more microconduits it is preferred to use image analysis that can distinguish a microconduit from the tissue in which a microconduit is formed. If a mask with microholes (FIG. 1) is used, then the edges of the microholes can be distinguished and used to identify the region in which microconduits are being formed (or were formed). Additionally, the edges of one or more microholes can be purposefully marked with distinct dyes so as to enhance the location of a region of interest (the area within a microhole).

If a collimated microparticle beam (FIG. 2) is used to form one or more microconduits, the image analysis means can be directed to the general tissue surface region. By using a previously calibrated beam size, the image analysis means can be constrained to look for localized areas corresponding to the beam size.

In an embodiment, a relatively inexpensive video camera with an image acquisition time in the range of between about one tenth (0.1) and about two (2) seconds can be used if the microconduit formation time is in the range of between about one (1) and about twenty (20) seconds, as this controls the microconduit depth to about ten percent. According to an embodiment, if a different depth resolution is desired, the ratio of image acquisition time to microconduit formation time can be chosen differently. The camera's spatial resolution need be only sufficient to resolve the localized area of a microconduit, so that the appearance of blood within the localized area can be detected. According to an embodiment, detection of blood within a microconduit by a video camera can be used with any method of microconduit or skin opening formation that is compatible with viewing of the microconduit or skin opening by a video camera.

In one embodiment, the process of forming one or more microconduits by microparticle impingement can be followed by the additional step of transporting one or more therapeutic molecules or ions through one or more microconduits to achieve drug delivery to tissue, including skin, for example.

In one embodiment, transdermal delivery of therapeutic agents (e.g., drugs such as insulin and genetic material such as DNA) is accomplished by forming a microconduit according to an embodiment of the invention, and then directing the therapeutic agent into the microconduit, thereby delivering the therapeutic agent through the skin to the tissue. In another embodiment, transdermal extraction of analytes is accomplished by forming a microconduit according to the invention and then removing the analyte from the tissue and through the microconduit, thereby removing the analyte from the tissue and through the microconduit. In one embodiment, the analyte is removed by sampling. For example, the analyte blood is removed by allowing the blood to flow out of a microconduit onto a collection sheet or plate. In another embodiment, an analyte such as interstitial fluid is removed by using, for example, a pipet to reduce pressure over the micro conduit.

Many other examples of drugs and genetic material are well known, including drugs such as lidocaine and other anesthetics, heparin, low, erythropoietin, growth hormone, steroids, various peptides, and genetic material such as large DNA segments, RNA, small antisense oligonucleotides, and immunological material generally, including vaccines and adjuvants.

Transdermal delivery of therapeutic agents through a microconduit according to an embodiment is important for a number of reasons, including the fact that often the intact stratum corneum prevents therapeutically significant rates of molecular and ionic transport. Microconduits according to an embodiment allow sterically unhindered movement of molecules and ions through the stratum corneum. The movement of molecules and ions through a microconduit according to an embodiment may take place through diffusion, electrophoresis, or convection flow driven by hydrostatic pressure differences, and time varying pressure differences including ultrasound produced and osmotic pressure differences. This includes iontophoresis which can involve both electrophoresis and electro-osmosis. In one embodiment, a direct current voltage is applied to a microconduit to produce iontophoresis. In a particular embodiment, the direct current voltage applied to the microconduit is pulsed.

According to an embodiment, molecular and ionic movement through one or more microconduits with varying degrees of control can be achieved by using different amounts or concentrations of the molecules and ions supplied. According to an embodiment, molecular and ionic diffusion can be controlled by controlling the supply concentration of the molecules and ions, controlling the solution (usually based on physiologic saline) used, and establishing or measuring the temperature, and then controlling the time that the supply solution is in contact with one or more microconduits. One embodiment of the invention utilizes diffusion of a therapeutic agent in a suitable pharmaceutical carrier, such as a biocompatible, non-toxic liquid, through microconduits to achieve transdermal drug delivery. In another embodiment, in order to achieve sustained release of the therapeutic agent, a therapeutic agent is supplied in a hydrogel, polymer, or molecular matrix, rather than in a liquid solution.

According to an embodiment, the invention relates to a method for forming one or more microconduits that allow desired molecular and ionic transport while substantially preventing the entry of infectious agents such as virus particles, bacteria and yeast. This exclusion of infectious agents is based on the formation of a molecular matrix within the microconduits. The openings within the matrix are generally small enough to block infectious agents or severely hinder the entrance of the infectious agents into the skin. A disadvantage of a molecular matrix is that it decreases movement of molecules and ions by convection flow because the characteristic size of the openings within the molecular matrix are small. However, movement of molecules and ions by diffusion, electrophoresis, and electro-osmosis, can still be achieved when a molecular matrix is used according to an embodiment.

Aqueous gels that are biocompatible and can exclude infectious agents while admitting ions and molecules are a suitable type of molecular matrix. Examples of gels are agarose, agar and carrageen. Polymer matrix gels can be positioned in contact with the skin by means of a pressure-sensitive adhesive with a rate controlling membrane or layer for the delivery of active molecules.

Another suitable gel is calcium alginate, which is gelled by exposing sodium alginate to an elevated calcium ($Ca^{2+}$) concentration. Thus, if $Ca^{2+}$ concentration is used to alter the recovery of a microconduit, the high concentration that tends to maintain a transdermal microconduit open is generally compatible with the use of a high $Ca^{2+}$ concentration to maintain a calcium alginate gel within a microconduit. Conversely, decreasing the $Ca^{2+}$ concentration near or within a microconduit tends to both encourage tissue recovery that will seal off a microconduit and simultaneously tends to dissolve the calcium alginate gel.

In addition to gels such as agarose, agar, carrageen and alginate which are obtained from natural sources, biocompatible polymer matrices obtained by cross-linking synthetic polymers can also be used. This includes polymers, which have been described for use in controlled release of drugs. This includes poly(L-lactic acid), poly(DL-Lactic acid) and copoly(lactic/glycolic acid). It is well known that the polymer matrix properties can be controlled by altering the polymer molecular weight or copolymer ratio (see Miyajima et al. "Effect of polymer/basic drug interaction on the two-stage diffusion-controlled release from a poly(L-lactic acid) matrix," *J. Controlled Rel.* 61:295-304, 1999). As another example, the transport of proteins out of a hyaluronate matrix was relatively slow for a fully esterified matrix but more rapid for a less esterified hyaluronate matrix (see Simon et al. "Mechanisms Controlling Diffusion and Release of Model Proteins Through and From Partially Esterified Hyaluronic Acid Membranes" *J. Controlled Rel.* 61:267-279, 1999). See also G. D. Prestwich et al. "Controlled Chemical Modification of Hyaluronic Acid: Synthesis, Applications, and Biodegreadation of Hydrazide Derivatives" *J. Controlled Release,* 53:93-103, 1998.

A variety of polymeric and bioerodable preparations suitable for implantation and subsequent release of bioactive material have been described in the scientific literature (see, for example, the review, R. Langer "Drug Delivery and Targeting" *Nature,* 392:55-S10, 1998).

The invention also relates to a delivery method and apparatus, such that immunizing material can be effectively introduced into the tissue near dendritic cells, and other cells such as keratinocytes, and then, as a further step, delivery into the dendritic cells, keratinocytes, and any other target cells within the skin.

According to an embodiment, the process of forming one or more microconduits is followed by the additional step of transporting immunizing material into the tissue. Cutaneous immunization in which immunizing material is delivered to dendritic cells within the skin is of particular interest. Thus, formation of transdermal microconduits that fully penetrate the stratum corneum can be followed by transport of immunizing material into the epidermis.

This process includes the transport or delivery of nucleic acids such as DNA into the skin for the purpose of cutaneous immunization. According to an embodiment, a solution containing nucleic acids is applied to the skin surface into which microconduits have been formed, and diffusion, electrophoresis or convection are used to transport nucleic acid molecules through one or more microconduits into the skin tissue. One or more nucleic acid molecules can also be transported through microconduits into skin tissue for the purpose of gene therapy.

In yet another embodiment, the method comprises the further step of creating an electric field so as to cause molecular transport with significant molecular transport component parallel to the stratum corneum but within the epidermis. That is, stratum corneum-penetrating microconduits made by any suitable embodiment of the method can be used to transport molecules into skin tissue; and suitable skin surface electrodes such as ring-shaped electrodes around one or more such transdermal microconduits can be used to create an electric field with a significant electric field component that is parallel to the outer skin surface (see FIG. 3). An electric field with a significant component parallel to the skin's surface thus causes lateral molecular transport within the epidermis by electrophoresis (electrical drift) and/or by electro-osmosis. Such lateral molecular transport is useful to deliver drugs and genetic material to skin cells away from the microconduits which are used to transport molecules across the stratum corneum. Such lateral electrical transport is in addition to lateral diffusion, which occurs within the tissue below the stratum corneum or below a nail.

In another embodiment, additional control with a generally faster response time is achieved by applying an electrical current or voltage across the tissue. In one embodiment, in the absence of a geometrically fixed, charged molecular matrix within microconduits, application of a current or voltage will predominantly produce molecular and ionic transport by electrophoresis, sometimes also called electrical drift. In the case of skin, transdermal drug delivery through at least one microconduit is thereby achieved by electrical drift (electrophoresis) as the transport mechanism. This can be achieved, for example, by providing an electrode near a microconduit, and another, more distant electrode at another site on the body. Alternatively, a tissue surface ring electrode can be placed with the microconduit opening within the ring.

According to an embodiment, once microconduits have been formed, therapeutic agents such as DNA or other vaccine material, for example, are provided at the outer surface of the stratum corneum of the skin, and directed into the openings of the microconduits. Then, according to an embodiment, one or more transport driving forces such as electrophoresis are applied, such that the therapeutic material or vaccine material is moved through one or more stratum corneum openings and thereby transported into the epidermis.

The therapeutic or vaccine material is transported substantially parallel to the outer surface of the stratum corneum, and may therefore encounter more immunizing cells than are located immediately adjacent the openings through the stratum corneum. In addition to electrophoresis, according to an embodiment, other suitable lateral transport driving forces include use of electro-osmosis, hydrostatic pressure gradients, sonic and ultrasonic fields, osmotic pressure gradients and concentration gradients.

Figure 3:
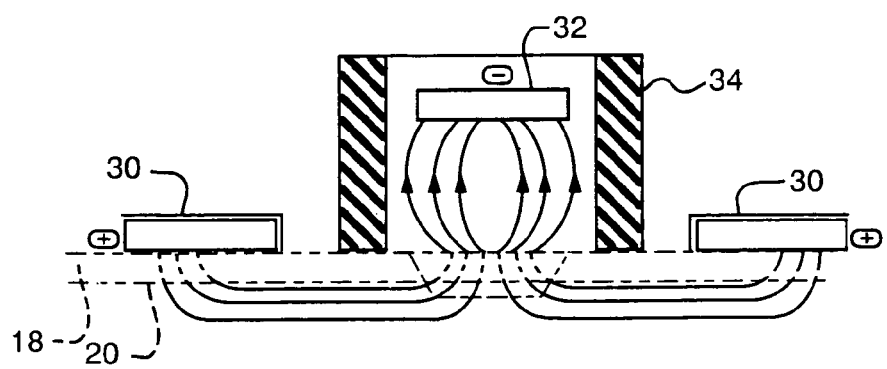
FIG. 3 is a schematic cross-sectional representation of an embodiment of the invention including a method and apparatus for electrophoretic transport of ions through a microconduit and into the epidermis.

FIG. 3 is a schematic representation of an electrophoretic method and apparatus, according to an embodiment, used to transport molecules or ions through a microconduit and into the skin and parallel to a major plane of the region of skin surface. In one embodiment, one type of electrode is positioned near, preferably substantially surrounding, an opening in a tissue such as the skin. In FIG. 3, the case of skin is shown, with a ring-shaped electrode 30 placed on the skin and surrounding a microconduit, represented by a dashed line indicating the outline of a tapered opening which comprises the microconduit. In the embodiment represented, the microconduit is wider at the outer surface of the skin, penetrates the stratum corneum completely, and terminates within the epidermis. The two cross-hatched vertical rectangles 34 indicate the cross-section of an electrically insulating short tube, within which is an electrically conducting aqueous electrolyte solution (not shown). A central, "inner electrode" 32 is located in a reservoir (details not shown) above this tube, with this electrode shown with negative polarity, suitable for electrophoretic transport of negatively charged molecules from the reservoir through the microconduit and thereby into the epidermis, where the field lines spread out. Some field lines penetrate deeply through the epidermis and into the subcutaneous tissue before returning to the outer, ring-shaped electrode 30, here shown with positive polarity. However, a significant number of field lines remain within the stratum corneum, and result in significant "lateral transport" of small ions and of charged molecules. This results in delivery of ions and molecules to regions of the skin away from the microconduit or other skin opening. This is particularly useful for delivery of DNA to the vicinity of cells within the epidermis that are somewhat distant from the microconduit or other stratum corneum openings.

In an embodiment of the invention, because of the size of the microconduits, liquid convection flow operates naturally to move molecules through a microconduit. Convection flow is important if no molecular matrix has been formed within the microconduit. In one embodiment, water soluble molecules are delivered by providing a driving force for convection through one or more microconduits. According to an embodiment, a pressure difference or pressure gradient is utilized to drive flow. For example, a pressure difference can be formed by applying an increased pressure with respect to the pressure within the tissue, at the terminus (entrance or opening) of a microconduit. If the surface opening of a microconduit is adjacent to a reservoir with a drug-containing solution of the molecule to be delivered, then increasing the pressure within the reservoir creates a pressure difference along the microconduit, and flow results. This is analogous to applying pressure to the solution within the barrel (reservoir) of a syringe: Increasing the barrel pressure drives flow through the needle (analogous to a microconduit) into a tissue. Thus, if transdermal drug delivery by convection through one or more microconduits is desired, flow can be established, according to an embodiment, by elevating the pressure in a drug reservoir that is held against the skin at the sites of one or more trans-stratum corneum microconduits. For example, in a particular embodiment, the drug or therapeutic agent directed into the opening is in a column, for example, a pipet or capillary tube, and the column is sealed to the tissue around the microconduit. Next, pressure is directly applied to the microconduit, for example, by squeezing a rubber bulb attached to one end of the column or pipet, thereby forcing the therapeutic agent included in the column or pipet into the microconduit. The therapeutic agent is absorbed by the tissue surrounding the microconduit. According to another embodiment, convection through microconduits can also be established by using an osmotic pressure difference, a time varying pressure difference such as ultrasound, and electro-osmosis.

According to yet another embodiment, pressure can also be used to force a deformable drug-containing hydrogel from a reservoir or supply into one or more microconduits. When inserted into a microconduit according to an embodiment, the hydrogel can provide slow, controlled release of drug into the epidermis, or into deeper tissues if the microconduit penetrates beyond the epidermis. Generally, molecules released into the epidermis migrate so as to enter blood capillaries. Other types of slow release entities of small size can also be introduced through microconduits.

According to an embodiment, molecular and ionic transport through one or more microconduits in the outward direction from the tissue can be used to acquire small samples of interstitial fluid, or a combination of interstitial fluid and intracellular fluid if cells are permeabilized or lysed, or blood if the microconduit extends sufficiently deep and accesses one or more capillaries or blood vessels within the tissue. Samples acquired by a method according to an embodiment can be presented to sensors or other measurement means located outside the body, and used for measurement or sensing of chemical analytes within the extracted fluid. Different types of sensors and assay systems which are suitable for sensing or measurement of the extracted sample have been developed by others and are well known in the art.

Transdermal extraction of small fluid samples for transdermal measurement is an important embodiment of the invention, and is accomplished by forming one or more stratum corneum-spanning microconduits through which a sample is transported for the purpose of carrying out a transdermal analyte measurement.

The invention also relates to a general process in which one or more analytes are measured while within a microconduit, rather than transporting the analyte out of the tissue to be measured by an external sensor or measurement means. For example, according to an embodiment, if a microconduit is formed in skeletal muscle, cardiac muscle, blood vessel wall or the liver, an optical measurement performed on fluid within a microconduit is used. This avoids problems associated with handling of very small samples, such as problems associated with dilution or contamination. Suitably small sensors can be inserted into a microconduit, or, preferably, optical measurement means such as near-infrared Raman Spectroscopy (see, for example A. J. Berger et al. "Feasibility of Measuring Blood Glucose Concentration by Near-Infrared Raman Spectroscopy," *Spectochim. Acta* 53:2887-292, 1997; T-W. Koo et al., "Reagentless Blood Analysis by Near-Infrared Raman Spectroscopy," *Diabetes Tech. Therapeut.*, 1:153-157, 1999; A. J. Berger et al. "Multicomponent Blood Analysis by Near-Infrared Raman Spectroscopy," *Appl. Optics* 38: 2916-2926, 1999) may be used.

According to an embodiment, to make an analyte measurement within one or more skin microconduits, the analyte can enter a microconduit from the tissue into which the microconduit penetrates, e.g., epidermal tissue. If the microconduit penetrates into a blood capillary bed and results in blood entering one or more microconduits, then the blood level or concentration of one or more analytes can be measured without transporting analyte through the microconduit out of the body. Instead, one or more analytes can be measured with the blood remaining within the body by virtue of the fact that the microconduit is within the body. This is particularly desirable if an optical measurement method is used. Artifacts and errors associated with nonblood tissue can be greatly reduced or essentially eliminated, because the blood is in full view of the optical measurement means such as reflectance spectroscopy, including near infrared Raman reflectance spectroscopy. An advantage of making a measurement within the microconduit according to an embodiment, is that exposure of healthcare workers to biohazards such as HIV or hepatitis virus is greatly reduced.

If natural or stimulated processes cause one or more microconduits to become significantly closed, such that transport of desired ions or molecules is significantly sterically hindered, then such partially recovered microconduits can be reopened to achieve useful levels of ion or molecule transport by application of pressure. Pressure can be essentially held steady, such as for example, by applying suction to open up a crust or initial formation of protective layer at the site of a microconduit. Alternatively, pressure can be applied intermittently, including in an oscillatory fashion. This includes the use of ultrasound.

In some cases a transdermal microconduit will become fully or partially blocked by lipids secreted from secretory granules that are involved in the skin's response to other types of stimulation. In this case, if the electrical resistance at the site of the microconduit becomes large due to blockage or coverage with lipids, one or more electrical pulses can be applied to form aqueous pathways through the lipid layers. The use of such electrical pulsing can also be combined with application of pressure.

This invention can also involve the additional step of providing a stimulus that causes cells to take up molecules such as therapeutic molecules and ions that have been laterally transported by an electric field with such a parallel (to the tissue surface) component. Stimuli suitable for causing such cell uptake within the epidermis include ultrasound, heating and additional electric field pulses which cause electroporation. An example of a cell that can be stimulated to take up a therapeutic agent is a dendritic cell. Examples of therapeutic molecules or ions that can be taken up by a cell are DNA and anti-neoplastic drugs. Finally, one or more electrical pulses are applied, such that at least one immunizing cell within the skin is electroporated such that vaccine material is delivered into at least one immunizing cell within the skin.

In yet another embodiment, it is possible to practice this invention without the step of providing lateral transport, in this case relying on delivery of vaccine material to the immunizing cells close to the stratum corneum openings.

The invention also relates to a method of forming microconduits through nail tissue.

EXAMPLE 1

Materials and Methods: An S.S. White Airabrasive unit (S.S. White Technologies, 151 Old New Brunswick Rd., Piscataway, N.J.), including a pressure chamber to hold an abrasive powder, was rebuilt. The pressure chamber was fitted with necessary valves, pressure regulators, and a hand piece on which a variety of nozzle sizes can be screwed; the pressure chamber was seated on top of a shaker. Using about 80 psi nitrogen pressure, microparticles were used to scission the stratum corneum of Subject A for about 12-15 seconds with the 500 µm diameter nozzle held stationary, and approximately {fraction (1/16)} inch away from his stratum corneum; no micromask was used. The microparticles comprised alumina or aluminum oxide abrasive powder, similar to what has been used in commercial units for facial peels. The microparticles were sharp, with size generally ranging between about 15 µm and about 20 µm, with some 30 µm outliers.

Results: Subject A reported a very slight sensation, and microscopic examination revealed a hole of indeterminate depth in his stratum corneum.

Method and Materials: The experiment was repeated, impinging the abrasive stream on a 250 µm thick, plastic micromask having 800 µm diameter holes. The micromask was taped to Subject B's left forearm on the palm side, and he waved the nozzle over pairs of holes in the micromask for time intervals of 10, 30 and 100 seconds at a distance of about ⅛ inch or 3000 µm between the nozzle and the mask.

Results: Nothing was visible on Subject B's stratum corneum in the 10 second case, but he could see capillaries in the bottoms of the microconduits made during the 30 and 100 second exposures. Furthermore, those microconduits began bleeding. The microconduits were slightly larger than the mask openings (microholes), and there may have been a swelling reaction up his forearm following the microparticle impingement. Subject B reported sensing a very slight "pricking" feeling only during the microscissioning process for the 30 and 100 second experiments.

The area along the forearm of Subject B where the holes were made showed signs of swelling. Later, a conclusion was reached that the swelling and inflammation were probably a sterile cellulitis, caused by the very aggressive use of 100 second exposure to the air jet with the microparticles, and that air was injected into the deeper tissue. Having thereby learned about "air injection injury," it was concluded that this could be easily avoided by using a combination of shorter exposures and smaller air pressure.

Figure 4A:
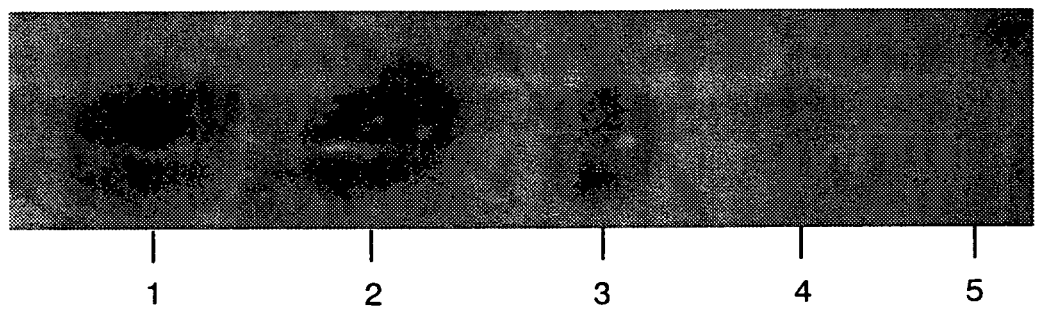
FIG. 4A and 4B are optical photomicrographs of microconduits formed according to an embodiment of the invention at six sites in the forearm of a subject individual, Subject B.
Figure 4B:
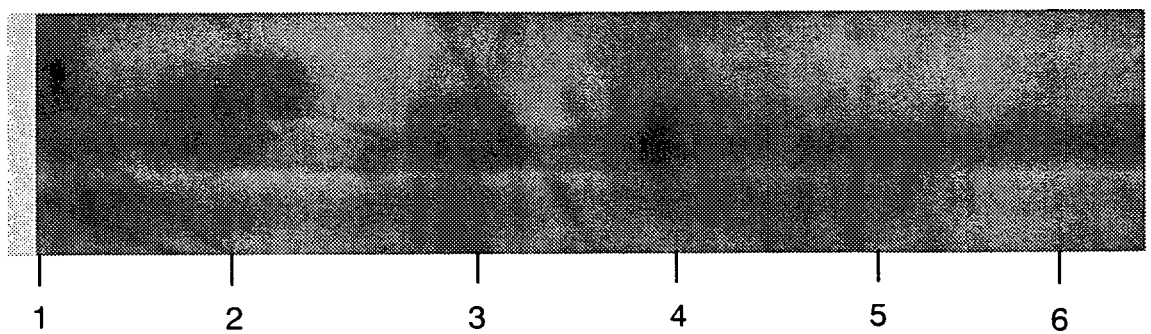
Figure 6A:
FIGS. 6A-6I include confocal images at different depths, indicated in μm from the approximate surface of the skin, of a forearm microconduit formed according to an embodiment of the invention in a subject individual, Subject A.
Figure 6B:
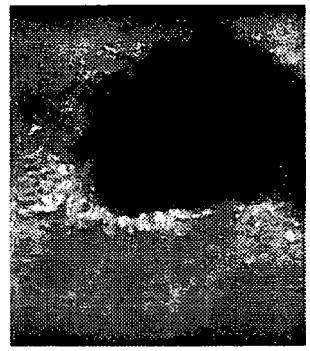
Figure 6C:
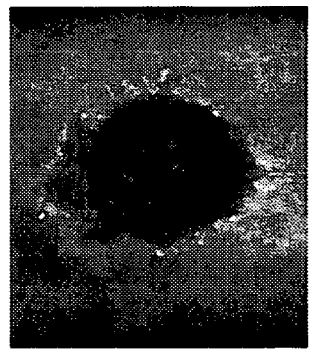
Figure 6D:
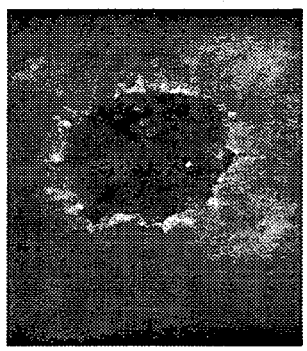
Figure 6E:
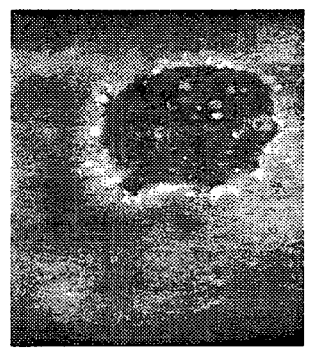
Figure 6F:
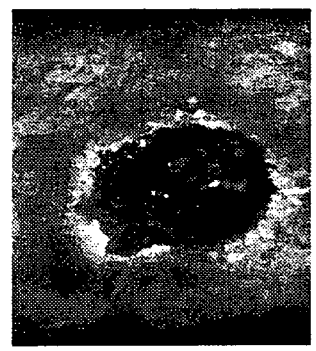
Figure 6G:
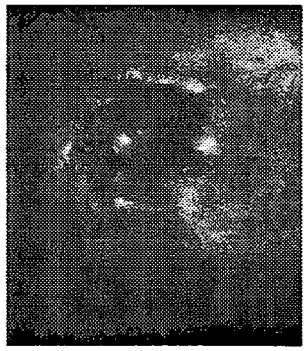
Figure 6H:
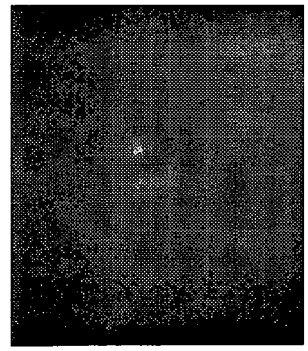
Figure 6I:
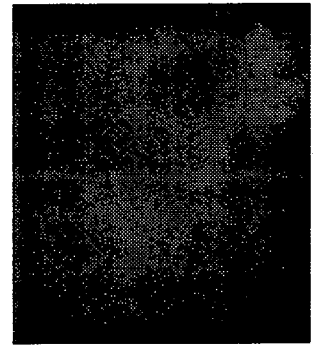

The white light images of FIGS. 4A and 4B are labeled with arrows marked 1 through 6. In FIGS. 4A and 4B, microconduits 1 and 2 are the result of the 100 second microparticle impingement; microconduits 3 and 4 of 30 seconds; and 5 and 6 of 10 seconds. In the black and white rendition of the original color photomicrograph, the blood drops at the sites of the two microconduits made by the 100 second exposure are dark gray, the smaller blood drops associated with the 30 second exposure are also gray, and the microconduits at sites 5 and 6 are not visible. It is believed that microconduits 1 through 4 fully penetrated the stratum corneum and epidermis, reaching blood capillaries, with blood flowing out due to normal blood pressure. However, the microconduits at sites 5 and 6 are believed to have not fully penetrated the epidermis (no visible blood; no visible mark or sign within the first few hours after formation of the microconduits.)

EXAMPLE 2

The experiment relates to the design of a mask holder to eliminate gaps between the mask and surface undergoing scission. Subject A recognized the need to have a picture-taking capability which would cope with the normal shake (tremor) of the human forearm, since the tremor is magnified in a microscope. He therefore obtained a frame grabber TV camera package and worked with a zoom microscope and laptop computer. Although not perfect, it makes much better pictures (via a computer and color laser printer) than were possible with the color instant camera used earlier.

Methods and materials: With this imaging improvement, Subject A began experiments with a micromask and microparticles. It was decided that holes on the order of 100 µm diameter on 500 µm center-to-center distances would be a reasonable place to start. Using 25 µm thick polyimide (PI) mask material, Subject A impinged microparticles to form four 100 μm holes. Holding this with a bandage that had a clearance hole of 1000 μm diameter, Subject A impinged microparticles onto the micromask for various times, up to 60 seconds with a nozzle having a 0.016 inch (400 μm) diameter opening.

Results: There was little or no penetration of Subject A's stratum corneum, although dust that was visible on Subject A's skin indicated that aluminum oxide microparticles clearly got through. Two things were noted. First, since the microparticles were in powder form, with grain sizes measuring 20 to 30 μm, it is likely that the microparticles were too big to get through the microholes in the micromask. Second, the thin PI mask, held against Subject A's skin with a bandage, did not touch the skin surface. Instead, Subject A's stratum corneum appeared to be pushed away by the bandage. This means that even if the microparticles got through, they did not hit the skin, but spread out, and the incoming air blast could actually "balloon" the stratum corneum pocket (region) under the PI mask. This in turn could produce a stagnating air bubble that would exclude most of the fresh incoming air and abrasive microparticles. It was therefore concluded that the mask needed to be tight against the stratum corneum, and much thinner than the hole diameter to permit air and microparticle exchange. Subject A then made a fixture, which acted somewhat like a drum head holder, with the PI mask stretched across it and held with double-sided sticky tape. The mask "drum head" surface protruded about 0.250 inch above the holding handle. With the micromask pressed into Subject A's stratum corneum, there appeared to be no space between the PI mask and stratum corneum. Subject A then used a 60 second sandblast at 80 psi through a 0.016 inch (400 μm) nozzle on a one hole (microhole) mask.

The above procedure opened up the hole in the micromask to about 5001 im rather than 100 μm. When the mask was used for microconduit formation, a clearly-defined hole (microconduit) was produced in Subject A's stratum corneum with no sensation. The microconduit looked moist at its bottom, and when squeezed slightly with tweezers, it bled. It was approximately 250 μm to 300 μm in diameter. It is likely that there were two effects. One is that, as with any open hole type of mask or stencil, the material coming through has no effect near the edges of the opening because of air stagnation (friction effect) and possible piling up of material in the corner formed by the mask, and the stratum corneum. This material "self masks" the stratum corneum near the edges. Second, the microholes must be some factor bigger than the microparticles going through them, or a dynamic blocking effect will occur wherein one microparticle nearly blocks or knocks an incoming microparticle away. Clearly, there was a 100 μm per side difference between the PI mask hole (500 μm) and the resulting hole in Subject A's stratum corneum (3001 μm).

EXAMPLE 3

The planned experiment was to test a confocal microscope, used to measure microconduits in vivo. The microscope, designed to look down through skin, uses a laser emitting 680 nanometer wavelength light as the light source, coupled with a TV framegrabber and precise vertical objective lens positioning. The wavelength of the illumination is such that materials with the refractive index of water are essentially clear or invisible, and materials with a refractive index away from that number are visible. For this reason the skin (mostly comprised of water) becomes essentially transparent, and the image is that of the materials that are not water, such as organics and inorganics at boundaries in the stratum corneum, and other materials located deeper in the skin tissue. Thus, with the confocal microscope and laser light source, one can view tissue changes that are several hundred micrometers deep in the skin.

Materials and Methods:

The plan was that Subject B and Subject A would each have an opening scissioned in their stratum corneum, to some depth shy of blood, and to use different microparticle impingement times in making the microconduits. More specifically, the plan was to form one microconduit per person, covered with a deionized water (DI) soaked bandage, then view the microconduits as soon as possible under a confocal microscope. A new, 75 μm thick PI mask with a 160 μm diameter hole was used. An electrical resistance meter, also referred to as an "impedance meter," was connected to two separate but adjacent conductive poles that were in direct contact with the skin. Both tests started with an ethanol rinse, followed by a deionized water wipe of the area to be impinged with microparticles. An EKG electrode was affixed to the subject between the mask fixture and the heel of the palm. The resistance of the skin between the EKG electrode and the area to be impinged was measured by means of an electrical probe immersed in conductive saline that covered the mask/microhole and the EKG electrode before, during and after impingement. The results are tabulated below.

| SUBJECT | Subject A Resistance | Subject B Resistance |
|---|---|---|
| DRY PI = Holder to EKG | 218 kohm | 1.2 Megohm |
| DI-I-suction-out Saline | 2.5 kohm 16 kohm (shunt) | 0.8-1.6 Megohm |
| Blow off Saline | 1.4 Megohm 170 kohm | 145 kohm |
| Suction-out saline DI rinse + blowoff | 2.3 Megohm | 600 kohm |
| 5 sec. Microscission SC @ 60 psi | 400 kohm | 3 Megohms |
| Saline Rinse: suction; blowoff Saline DI rinse | 160 kohm (possible shunt) 2.9 Megohm 216-218 kohm 2.5 Megohm | 5 kohm (shunt) 2.6 Megohm 20 kohm 1 Megohm-(No blood visible) |
| 5 sec. Microscission SC @ 60 psi | 2.5 Megohm | |
| Saline Double DI rinse, suction | 30 kohm .4 to 1.2 Megohm Subject A - (Blood visible) | |

SC = Stratum corneum
DI = deionized water

The sites on each wrist were marked with small, inked-in lines. The maskholder was cleaned with ethanol between Subject A and Subject B tests. The sites were covered with bandages soaked in DI water. A confocal microscope described above was used to examine Subject B's site first. The time period between the test and the confocal examination was approximately one hour.

Results: The opening of the microconduit at the top of the stratum corneum was on the order of 100-125 μm. The depth was in the range of 130 μm. There was particulate debris lying on the surface and in the hole. It was difficult to determine the depth precisely, because illumination in the hole was poor. This was due in part to the back reflection being suppressed by the non-planar surfaces at the bottom of the hole. At depth, back reflection was further suppressed by the form factor (depth to diameter ratio) causing increased collimation which reduced the back reflection even more. However, the confocal microscope worked very well, showing the cross sections of the hole, as made by the microscissioning process, at selected depths. In general, the microconduits tapered to half diameter at their bottoms, in the outline of a blunt-bottomed carrot.

FIGS. 5A-5K include Subject B forearm microconduit confocal images at different depths (indicated in µm from the appropriate skin surface), starting at zero, and going to a depth of 170 µm. Note that deeper than 79 µm, there is less evidence of a microconduit.

Three percent (3%) lidocaine was applied on the Subject B site. No discernible anesthetic effects were observed.

The examination of the Subject A's stratum corneum showed similar effects. The diameter at the stratum corneum was also in the 100-25 µm range. The depth was approximately 175 µm. The blood clot in the Subject A microhole was invisible with the confocal microscope. There appeared to be debris at the bottom of this hole also, as small (20/30 µm) spherical objects could be seen.

FIGS. 6A-6I include Subject A forearm microconduit confocal images at different depths (indicated in µm from the approximate skin surface).

EXAMPLE 4

A fungus is sometimes found to live in the interface between nails (in particular, toe nails), and the underlying living tissue. Such infections tend to be chronic, since it is difficult to treat topically due to its protected location. An established treatment in serious cases is removal of the nail(s) to reach the fungus. Therefore, an experiment in making through-nail microconduits, to permit application of topical antifungal chemicals, was performed.

Materials and Methods:

Microparticle impingement was achieved using a "particle generator", which was a custom modified S.S. White Airbrasive Unit, Model K, Series II (Piscataway, N.J.). This apparatus occupies a cubical volume of approximately 14 inches on a side, and contains a solenoid-driven table, onto which is bolted a pressurized reservoir with a spring-loaded top, through which the microparticles can be loaded into the reservoir. A tight fitting, 1.5 inch diameter.times.0.5 inch plate, with a hollowed-out region, creating a circular particle/gas mixing chamber, was used. Carrier gas was admitted through a hole in the chamber wall, and exiting through a second hole in the wall, approximately 120°s away from the input. The thin top of this chamber served as the bottom of the reservoir, and contained a number of small holes through which (microparticles) could fall into the swirling gas stream of the chamber below. The particle chamber and mixing chamber were at the same pressure. From the mixing chamber the particles/gas flow proceeded through a flexible plastic tube, which terminated in the nozzle holder. Various sized tungsten nozzles can be screwed onto this nozzle holder, and act to direct and size the particle stream. The unit also contained a power supply and meter to change the shake table amplitude, which increased or decreased the flow of the particles into the gas stream. Also there was a pressure gauge and pressure regulator to monitor and set the gas pressure.

It should be noted that the air pressure used in this example (20 psi) was much lower than the pressure used for industrial applications with this machine. Further, the amount of particles in the flux of particles was much less than the amount of particles used in other applications. It should also be noted that having very few particles going into the flux works better than having many particles going into the flux. Otherwise, in forming a microconduit, a high concentration of particles in the flux will tend to pile up in the tissue, rather than microscission and remove tissue.

Viewing and measuring the microconduits was accomplished with a Bausch and Lomb Stereozoom 7 microscope with a variable magnification (2×-7×). A measuring eyepiece was used to check planar dimensions. A Panasonic CCD television camera with a 0.75×-3×lens connected to a 15 inch color monitor was used to view regions of test material, skin or nail before and after microconduit formation protocols. The monitor was calibrated against a vernier caliper projection (image), with marks hand drawn onto the monitor screen. This could also be connected to a computer having a frame grabber (Visionx), which allows the image to be viewed and recorded on a floppy disk for making color photomicrographs.

Microparticle impingement was carried out using the 0.011 inch nozzle at 20 psi and 70 v flow (setting on the S.S. White machine), spaced approximately 0.030 inch between nozzle and nail surface. The 0.125 inch or so of overhang edge of the nail on Subject A's left little finger was used.

Results: That area of the nail, 0.020 inch (500 µm) thick, was scissioned through in 15-20 seconds (best estimate is 16 seconds). Because no mask was used, the microconduit was larger on the nozzle side and tapered to 0.010 inch diameter on the far side of the nail. The microconduit opened quickly, possibly because the nail is much harder, less "bouncy" than the stratum corneum, and the nozzle was half as far away from its surface.

The experiment was repeated on another area, but this time, Subject A scissioned part way through the nail, and put some black ink in the resulting "cup" (depression or incomplete microconduit) to see if it would soak in, or diffuse beyond, the dimensions of the "cup." It didn't—there didn't seem to be any lateral diffusion of the ink at all, which was surprising, as nails are brick-wall like, in the same fashion as the skin's stratum corneum, only much thicker.

Although not then known to Subject A, it would be useful to know what chemical indicators might exist to determine how close to the nail's bed the microconduit has approached. Clearly, the microconduit formation rate difference between stratum corneum and nail (somewhere between a ratio of 7 and 15 to 1) means that the microconduit formation might well "self-limit" (stop) when the softer substrate (underlying tissue) is reached. It acts like the skin that isn't beneath the nail. To know when to stop impingement, one could rely on the "sensation" indicator (a small prickling feeling or the appearance of blood), but there may be other indicators possible. A question raised was, how close does a microconduit have to extend through the nail to deliver drug for effective treatment of the fungus?

It was recognized that it would be useful to devise a fixture to hold the nozzle a fixed distance above the nail. It is important to stabilize the nozzle to nail spacing, and also tie the nozzle to the nail's motion. Trying to place the finger on a flat surface under the fixed nozzle relies on the spongy finger pad, which clearly leads to too much motion over a 10-20 second time interval. This fixture probably should be strapped onto the nail, like a saddle on a horse, with the nozzle held rigidly to this frame.

There are many potential applications for nail microconduits, in addition to treating fungus. For example, identification numbers could be formed, using standard Arabic numbers, bar codes, digital codes, or the like. The removal of less than full depth would allow one to "write" on the nail surface. This may also find cosmetic application, in which people write the initials or names of friends and loved ones, perhaps with coloring (dye) added to the "etched" region. Within a few weeks, the outgrowth of the nail would carry such markings away, to be removed with nail trimming.

For cosmetic purposes, a light scission by microparticle impingement could improve the adherence of a faux nail to the real nail. Bas reliefs can be engraved in the nail surface, and dyed. One could possibly put in dye at various levels by partial excision, dying, then scissioning a little deeper and dying a different color below, for example.

EXAMPLE 5

Lidocaine 2

This experiment involved creating a transdermal microconduit followed by delivery of lidocaine to attempt achievement of localized anesthesia.

Methods and Materials: A single microconduit anesthetic experiment using fifty percent (50%) Lidocaine was conducted. The modified S.S. White apparatus was used with a setting of 35.7 Volts, 25 psi. With these settings, a microscission-through time of 18 seconds was established in test material. The mask was a single 170 microhole in 3 mil kapton. The preparation protocol included application of ethanol, a DI water soak, and drying. The initial resistances were Dry—open (open circuit; very high resistance), Saline—230K (Kohm), Suction out/DI rinse—open.

Microscission by microparticle impingement was carried out for 10 seconds, which would give a microconduit depth that was clearly through Subject A's stratum corneum, but would not exceed 50-70 μm, based on the recent data from the confocal microscopy experiments.

The resistance was Dry—open, Saline-11 Kohm (a significant decrease) and Suction out/DI rinse—open. Cotton swabs were soaked in the Lidocaine solution, and one was placed on a control (non-microscissioned) stratum corneum control site, and the other on the microconduit, which was clearly visible under the microscope. A swab was held on the microconduit site for 2 minutes. A second swab was held on the control site for 2.5 minutes. A new No.22 hypodermic needle was used to prick probe to determine existence of sensation.

Results: A slight pressure on touching the stratum corneum with the point produced sharp sensation. Using a scale divided into 32nds of an inch (0.031 inch), Subject A pricked his stratum corneum at different radial distances from the microconduit. His skin was numbed to the point of no sensation for approximately 0.015 inch (half a space), and then sensation was clearly felt around the {fraction (1/32)} inch distance and farther out. Subject A could not state that at the {fraction (2/32)} inch marker there was any different sensation level than untreated stratum corneum (if it did, it was insignificant). Subject A thought that the region around the microconduit became more numb 4 or 5 minutes after the treatment. The numbness began to diminish after 9 minutes. The treated control site showed the same level of prick sensation as a nontreated site.

EXAMPLE 6

Lidocaine

This experiment involved creating a transdermal microconduit followed by delivery of lidocaine with applied pressure to augment transdermal drug delivery, in this case for achievement of localized anesthesia.

Subject A used a standard pin, which is slightly duller than the hypodermic needle, but can still be felt clearly, and doesn't damage the stratum corneum or outer epidermis as much as the sharp needle. 10 mg epinephrine added to a 20 ml saline +1 gram lidocaine (50% lidocaine) mixture was prepared.

Initially, when trying to calibrate the modified S.S. White "microparticle generator" before the experiment, the test microscission rates in 2 mil kapton strips were extremely erratic, but then became stable. Then, with a microscission time through 2 mil Kapton of 24 seconds (33.46V), Subject A used the same 150 μm diameter single hole mask on the new maskholder for the experiment below, with 8 second impingement time.

| | Resistance |
|---|---|
| Dry = | 125 K kohm |
| DI water = | 1.5 Meg (Meg = Megohm) |
| Suction out; blow out = | 124 kohm |
| Saline = | 150 kohm |
| SO (suction out) = | 213 kohm |
| DI = | 500 kohm |
| Suction out = | 115 kohm |
| DI = | 450 kohm |
| Suction out, Blow out = | 150 kohm |

Scission by microparticle impingement was conducted for eight (8) additional seconds; at first obtaining a slight amount of clear fluid, and later a very slight amount of blood.

| | |
|---|---|
| DI = | 105 kohm |
| Suction, Blowout = | 560 kohm |
| DI = | 800 kohm |
| Suction, Blowout = | 250 kohm |
| Saline = | 6.3 kohm |
| Suction, Blowout = | 300 kohm |
| DI = | 115 kohm |
| Suction, Blowout = | 360 kohm |
| Saline = | 6.5 kohm |
| Suction, Blowout = | 300 kohm |
| DI = | 500 kohm |
| Suction, Blowout = | 200 kohm |

An attempt was made to increase the delivery of 50% Lidocaine+epinephrine (the "drug") through the microconduit by applying pressure to the outer (skin surface) opening of the microconduit. The following results for the increase in numbed area are:

| Drug | Water pressure | Pinprick numb radius |
|---|---|---|
| 1 min. | 30 inch | 400 μm |
| 2 min | 30 inch | 800 μm |
| 3 min | 30 inch | 1600 μm |
| 6 min | 30 inch | 2800 μm |

Results: First, there was no observable blanching of the stratum corneum/epidermis around the microconduit site. Subject A tried the same pressure, the same drug (lidocaine-epinephrine) on another (control) site (no microconduit) to check possible changes, but could really see no difference from the surrounding skin. But his skin pigmentation was "white", so any blanching may have been difficult to discern. Also, it's possible that the epinephrine didn't really reach enough capillaries, or that near-stratum corneum capillaries don't respond the same way as deeper blood vessels.

Second, testing with the pinprick approach yielded the same results as before. However, Subject A continued pin pricking to find that approximately 6 (six) minutes after the last injection (introduction through the microconduit), the radius of numbness was in the vicinity of 2800 µm. This outer limit began shrinking after 10-12 minutes. Thus, there seemed to be an additional anesthetic spreading effect for about 6 minutes.

Third, Subject A tried electrical stimulation as a test of the extent of anesthesia. He used 200 volt, 2 ms, 30-40 mA pulsing (two pulses per site) after discovering the 6+minute lateral spread effect. The site was numb to the electrical pulses within a 1400/1600 µm radius. Previously there was only slight sensation to the electrical pulses near the microconduit, much less than in non-anesthetized regions. With pressure-driven delivery through the microconduit, however, these strong electrical pulses weren't sensed, suggesting delivery was to a greater depth (and greater extent laterally) over the 6 minute period.

EXAMPLE 7

Glucose 1

This experiment involved creating a transdermal microconduit to produce a blood sample that would be then used for a blood glucose measurement.

Methods and Materials: The experiment is intended to measure blood glucose, using a commercially available device that can measure glucose in a drop of blood. The measurement device is a "Lifescan" "Fast Take" Glucose Sensor, with a readout contained in an oval case approximately 1.5 inches×2 inches by ⅜ inch thick. On one edge is a slot into which is plugged that 0.031 inch×0.210 inch×1 inch sampling strip. This is plastic, has three electrical contacts on the plug in end, and a small capillary, 0.1 inch×0.1 inch×0.010 inch, in which appear to be two electrodes, or gel areas, each of which are 0.1 inch×0.05 inch, one in front of the other, so that the blood being pulled into this chamber by capillary action must cover all of the first before beginning to cover the second. Once the sample chamber is filled, the electronics takes 15 seconds to display the glucose level (50-200 mg/dL).

Subject A carried out a 16 second microlocalized microparticle impingement, using a mask with one 150 micrometer microhole, to form a microconduit that should reach blood capillaries. Subject A squeezed around the microconduit once in the x-x direction, and once in the y-y direction, obtaining enough blood to fill the rectangular capillary/measuring chamber for the measurement device.

Results: The instrument took 15 seconds to respond, and displayed 97 mg/dL for Subject A's glucose level, which is a normal value. This procedure was very simple and easy. There was little sensation.

EXAMPLE 8

Glucose 2

This experiment also involved creating a transdermal microconduit to provide a blood sample that would be used for a blood glucose measurement.

This experiment again used a commercially available device (the "Lifescan" "Fast Take" Glucose Sensor) that measures glucose in a drop of blood.

A 10 second (microparticle impingement) exposure on the arm of Subject A was conducted, to determine how much less exposure time would work in measuring the blood glucose level.

Results: The electrical resistance after exposure was 50 Kohm, and microscopic examination through the mask showed little redness, so Subject A did another 10 second exposure to make sure that blood vessels had been reached. Blood was indeed obtained, and the electrical resistance was now 7.7 Kohm. Blood flowed out. Subject A used a test strip that came with the kit in the meter, but it's detector looked different. It had a detector area twice as long as the prior strip, and there was no clear cover over it, so it couldn't draw out blood by capillary action. Instead, a blood drop had to form, and be dropped in the sample area of the test strip or the test strip laid face down in it, rather than have the end edge dipped in and the blood suck up into the capillary. There was enough blood to get a reading of 107 mg/dl. As with Example 7, the sensation detected was just slightly discernible.

EXAMPLE 9

Nail 1

This experiment involved measurements of the rate of microconduit depth formation ("scission" rate).

Materials and Methods—Additional experiments use "cantilever clippings" from Subject A's toe nails. These toe nail specimens behave the same way as finger nails, with nearly the same scission rate (0.00075 inch per second). To further determine the rate of microconduit depth formation more toe nail clippings were used.

Microlocalized scission (microconduit formation) was carried out in experiments on Subject A's toe nail clippings, with the results shown below.

TABLE

| Subject/experimenter: Subject A/Subject A | | |
|---|---|---|
| Thickness at microconduit | Time (sec) | Scission rate (in/sec) |
| TOE 0.015 inch (375 µm) | 15 | 0.001 |
| 0.025 inch (625 µm) | 35 | 0.0007 |
| 0.030 inch (750 µm) | 51 | 0.00058 |
| 0.042 inch (1,050 µm) | 210 | 0.0002 |
| FINGER 0.017 inch | 17 | 0.001 |

Results: Based on previous experiments, there were no surprises. The decrease in scission rate (microconduit depth increase rate) with thickness was perhaps due to "self masking" of incoming microparticles competing with backbouncing microparticles, with this competition increasing with increasing form factor. Based on present understanding of the microconduit formation process, the major source of variability is due to the nozzle angle to the nail surface.

Some variations of the particle generator parameters were considered next. The nozzle-to-nail surface space was always 0.030 inch.

1. Vary pressure on a 0.016 inch (400µ) thick finger cantilever (flow setting=85V, as in past tests):

| Pressure (psi) | Time (sec) | Scission rate (in/sec) |
|---|---|---|
| 15 | 34 | 0.00047 |
| 20 | 16 | 0.001 |
| 25 | 12 | 0.00133 |

Vary pressure on a 0.016 inch (400µ) thick finger cantilever (flow setting=65V, changed from past tests):

| Pressure (psi) | Time (sec) | Scission rate (in/sec) |
|---|---|---|
| 15 | 25 | 0.00064 |
| 20 | 21 | 0.00076 |
| 25 | 15 11 | 0.00107 |

Again, with the exception of the 15 psi (lower flow result), there were no surprises. The low flow (65V setting) test was repeated twice, with nearly identical results. Perhaps it is worth exploring the lower flow, lower pressure regime, as well as higher pressure. Since, however, sensation appears not to be a problem, it might to be reasonable to increase the pressure to achieve faster microconduit generation into the nails. In both the above tests, the microconduits measured 20/22 mils at the "top" (outer) surface and 15/16 mils at the bottom side.

All these tests were done with the nail clippings held in a fixture with their "outer end"(outer surface) up, as if the hand were held vertically. The nozzle was located on a second fixture, with microparticle impingement horizontal. Both holders (nail specimen holder and nozzle holder) were mounted on x-y-z manipulators, with theta rotation to permit the nozzle to be positioned (by eye) perpendicular to the nail's "outer" surface. this arrangement allowed one to observe the back (former inner surface) of the clipping while scissioning, to see when the through-microconduit (penetrating microconduit) first appeared. One could also shine a light at the nozzle side to make the penetration process easier to observe. However, it turned out that the best indicator was that of a microparticle pattern ("dust") appearing on the floor beneath the nozzle/nail arrangement, scattered by the nitrogen gas stream coming through the nail, rather than bouncing back from the outer (front) surface.

In looking at one of the test fingernails, it was noticed that there was a good display of the kinds of microconduit centers one can achieve. The dimensions of Subject A's nails are,

| | |
|---|---|
| Little = 0.350 inch W (width) × 0.300 inch L (length) | |
| Middle = 0.450 inch W × 0.400 inch L | |
| Thumb = 0.550 inch W × 0.400 inch L | |

All measurements are 90% of the maximum dimension. This means that if one can easily open microconduits on centers from 0.020 inch or greater, it is possible to span nails with properties like those of Subject A with anywhere from 5 to 20 microconduits of 0.015-0.017 inch maximum diameter. If one wanted to form a full field of microconduits, it would require 25 to 360 microconduits, as an example.

In another application, one could think of a nozzle being driven X-Y by stepping motors which interface with a computer programmed with a simplified image converting or numerical control machining program. One could sculpt a variety of images, numbers, and pictures within a few minutes per nail. In the case of complex images, the computer program could also modulate the flow and/or pressure to produce depth variations which would enhance the "dimensionality" of the sculpture.

A check was done on high pressure $N_2$, at 30 PSI, 85V flow setting, 0.030 inch nozzle-nail spacing, and the through-microconduit time was 9 second on the 0.016 inch thick part and 11 second on the 0.018 inch thick part of that nail. This corresponds to 0.0018 inch/second and 0.0016 inch/second.

EXAMPLE 10

Nail 5

This experiment involved measurements of electrical resistance associated with nail microconduits, and commentary related to antifungal treatments.

Electrical resistance measurements have been used in an embodiment of the invention to partially characterize skin microconduits. At this point, it had been two weeks since the first microconduit accessing blood was formed in the left hand ring fingernail of Subject A. However, we anticipated that there would nevertheless be a large resistance decrease associated with the microconduit, because insignificant nail repair was expected, and other protective layers that form should have a much smaller electrical resistance than the nail.

Materials and Methods: The LCZ meter (a device for measuring electrical resistance and impedance in skin or transdermal microconduits) parameters were the usual 1 V, 1 KHz. All resistance tests were checked for greater than 5-10 Megohm "before test" readings. At these resistance levels, Subject A took special precautions to isolate himself, from anything, especially shunting to the EKG (ECG, electrocardiograph) electrode, through his right hand that was holding the Tungsten (W) probe, a small, stiff electrically conducting wire that could be inserted into a microconduit. The tungsten wire was wrapped around a 6 inch long plastic rod, which Subject A held in a glass hypodermic syringe while wearing a plastic glove. Subject A always kept his left hand/arm elevated from the table during the tests. Results of the experiment are summarized in the following table.

| Results and Analysis: | Resistance |
|---|---|
| 1. 2-0.005 inch diameter Tungsten wires in Saline = | 2.2 kohm |
| 2. EKG in saline, W wire in saline = | 1.3-2 kohm |
| 3. EKG on LH middle finger tip, EKG in Sal on = middle finger | 11 kohm |
| 4. EKG on LH middle finger tip, EKG on LH ring = finger tip | 35 kohm |
| 5. EKG on W wire touching stratum corneum on = Ring fing., | 1.5-15 Megohm |
| 6. EKG on W touching DI drop on stratum corneum = on Ring fing. | >500 kohm |
| 7. EKG on W touching stratum corneum in DI drop on = stratum corneum on Ring fing. | 130 K-150 kohm |
| 8. EKG on W touching Sal drop on Stratum corneum = on Ring fing. | 31 kohm |
| 9. EKG on EKG on LH ring finger nail = | 500-550 kohm |
| 10. EKG on W in Sal on LH ring finger nail = | 500 K to > 10 Megohm |
| 11. EKG on W in DI H20 on LH ring finger nail = | 260 kohm |
| 12. EKG on W in Sal. Drop in large microconduit = to nail bed | 130 kohm |
| 13. EKG on W in Sal drop in microconduits to nail = bed and near nail bed | 120 kohm |

From these measurements it is clear that the two microconduits in Subject A's LH (left hand) ring finger nail have led to a factor of 5 reduction in the EKG-on-LH-nail-to-EKG on LH middle finger tip resistance (9, 12. & 13, above). A clean, "saline in small microconduit only" measurement, could not be obtained because this microconduit was close to the large microconduit.

A review of relevant information about nails appears in, "The Nail", Vol. 1, Physiology, Biochemistry, and Molecular Biology of the Skin, Second Ed., 1991 Lowell A. Goldsmith, Editor, the teachings of which are incorporated herein by reference in its entirety. The term "nail" usually refers to the nail plate, which is a hard, clear to whitish, rectangle of tissue on the dorsum of the distal phalanx. In order to design an in vivo experiment to determine whether placing fungus-killing chemical compounds into one or more microconduits through a toe nail, some additional information may be needed. Clearly, however, a microconduit removes essentially all of the barrier function of the nail. With this in mind, a general review of the nail size and thickness on the left side of Subject A was determined.

|  | Little | Ring | Middle | Index | Thumb |
|---|---|---|---|---|---|
| Left Hand |  |  |  |  |  |
| Length | 0.300 inch | 0.350 inch | 0.350 inch | 0.400 inch | 0.425 inch |
| Width | 0.350" | 0.450" | 0.475" | 0.375" | 0.550" |
| Thickness | 0.016" | 0.017" | 0.018" | 0.021" | 0.026" |
| Left Foot |  |  |  |  |  |
| Length | 0.100 inch | 0.225 inch | 0.350 inch | 0.350 inch | 0.550 inch |
| Width | 0.325" | 0.325" | 0.400" | 0.375" | 0.550" |
| Thickness | 0.025" | 0.025" | 0.039" | 0.036" | 0.053" |

It is clear to see that the toe nails are thicker than finger nails by a factor of 1.5 to nearly 2. That means that toe microconduits will be bigger than have been found previously by us for finger nail microconduits, where fingernails have been tested—mask or no mask—because the undercut in a 0.030 inch-thick nail will tend to produce a microconduit approximately 0.020 inch diameter, minimum, even if a mask with a 0.006 inch diameter is used. In addition, even with no mask, the microscission-through time would be in the range of a minute or more per microconduit. The approach in the experiment was to carry out microconduit tests without a mask. Toe nail sizes are both bigger and smaller than fingernails, which will perhaps require several different sized nozzle holder "saddles."

The question of whether to form many microconduits in a nail, located, for example, on centers twice the microconduit diameter, was considered. An alternative, exemplary approach is to form a line of microconduits across the nail, back towards the lunula. It is believed that fungi only grow on dead material. For this reason, the under-nail fungal infestation is living on the nail only, not the nail bed, nor on the nail-originating tissue known as the nail matrix, which is beneath the skin, and under and behind the cuticle, and somewhere out into the vicinity of the lunula. With all this in mind one application of the invention may involve a line of microconduits across the lunula edge of the nail, with the microconduits acting as reservoirs and "sweeping" the fungus out as the nail moves out.

Antifungals useful in an embodiment include non-prescription drugs such as tolnaftate including Tinactin®, or Miconazole Nitrate Cream USP, 2% (E. Fougera & Co., Melville N.Y., 11747), Terbinafin, or prescription antifungal drugs such as Penlac®. The non-prescription drugs are typically used as topical applications to kill and/or block replication of dematophate fungi which cause "onychomycosis", which causes ringworm and athlete's foot (tins pedis). With the present exception of Penlac®, there is no approved topical drug for treatment of nails, presumably due mainly to the inability of significant drug to reach the site of most of the fungus. The active ingredient of Tinactin® is tolnaftate; Miconazole nitrate is itself the active ingredient of the second nonprescription cream-form medication.

Penlac® is used to attempt to kill the same fungus when it occurs between the nail and nail bed. It is used in the form of a laquer containing the antifungal chemical "ciclopirox", typically provided in solution at 8% concentration. Loprox® is another antifungal preparation, which has the same antifungal agent (ciclopriox) except at a smaller (0.77%) concentration, which is available in cream, lotion or gel combinations for treatment of superficial dermatophyte infections. Still another medication is NonyX, an over-the-counter keratin-dissolving preparation containing 9.5% ethanoic acid. It is claimed that this preparation can penetrate the nail and selectively attack keratin debris, which is the habitat and food supply of the fungus. Like the other two, it involves a long treatment, requiring approximately 4-12 months to eliminate fungus under nails, and is effective in only a fraction of patients.

Because the available medications are intended for use under conditions where drug does not have ready access to the fungus, it is not presently known what amounts and concentrations of such drugs should be used with delivery through microconduits. For example, the usual preparation containing ethanoic acid may be too strong for direct application through nail microconduits. In the examples of Penlac® and Loprox®, both contain ciclopirox, but the need for soaking through the nail may have required that the antifungal percentage be increased by a factor of 10 over the Loprox®, in order to deliver an adequate amount to the nail bed, to access the fungus under the nail. Since Loprox® is specifically intended for topical use on skin, of the examples considered above, perhaps it would be a good candidate for application through the nail microconduits. Tinactin®, containing the drug tolnaftate, and used for athletes foot, is also a good initial candidate for use with nail microconduits, since it presumably isn't too irritating in the case of direct dermal application.

Determination of how much of each drug should be applied at what time intervals through various numbers of microconduits can be investigated using existing methods of clinical study. The microconduits will act additionally as drug reservoirs, such that the nail bed at the bottom of each microconduit will be exposed continuously to the drug. In general, prolonged contact with various drug preparations are desired and acceptable. Depth and spacing of microconduits determine where the drug will diffuse, and whether it can also be transported by a pressure difference and electrical fields. If needed, residual drug within a microconduit could be removed at intervals, and replaced with fresh drug containing solution, cream, lacquer or gel.

Microconduits can be covered with simple, protective materials such as plastic sheet with adhesive, nail polishes, lacquers and the like, or left open to the air. Such covering could be removed, for example, upon bathing, which would tend to wash out the microconduits, that could be reloaded and recovered. Alternately, microconduits can simply be left "open."

EXAMPLE 11

Nail 6

This experiment included forming microconduits in the toe nails of Subject B, who had a persistent toe nail fungal infection.

Materials and Methods: A clipping of a nail on Subject B's left middle toe, which was 0.024-0.025 inch thick, was made. Conditions for microconduit formation experiments included a pressure of 25 PSI, flow setting of 85V (85 volt) for the microparticle supply device (the custom modified S.S. White machine described earlier), and nozzle-to-nail spacing of 0.030 inch (these parameters used for the following experiments). It was determined that 24-26 seconds were needed to scission a microconduit through a clipping by microparticle impingement. The corresponding microconduit depth increase rate was about 0.001 inch (25µ) per second, which is similar to what was found previously for Subject A's finger nails.

Next, the "saddle" device was attached to Subject B's LH big toe nail, which had a good sized overhang ("cantilever"); also much of the nail was detached (lifted up) from the nail bed due to the fungal condition. The goal of this experiment was to form a microconduit through the overhang portion of the nail, and to determine the corresponding scission rate. The scission rate was about one mil per second, and the microconduit diameter was around 25 mils at top. This gave an initial bench mark scission rate for Subject B's nails.

Results: Subject B then selected a spot near the good-sized overhang on his right big toe, where the nail was well adhered to the nail bed and very near the edge of the overhang. It was decided to (microlocally) scission to a certain depth there, hopefully just getting through the nail, and therefore a microconduit which reaches just to the bed (top surface of the living tissue under the nail). This nail overhang measured 0.032-0.033 inch thick nearby, so the goal was to approximate that time, assuming from the test scission rates that it was possible to just reach the bed. Using the marked and calibrated hypodermic needle "yardstick" (microconduit depth probe) it was determined that the hole was 800 µm deep. This means that either the nail is thicker where it adhered to the bed, or its scission rate is slower when the nail is healthy and adhered to the bed. In measuring the hole depth, Subject A pressed the slightly blunted microconduit depth probe tip into the bottom. It was unyielding, feeling like it was being pressed on nail material, unlike how it felt against the bottom of Subject A's "shallow" LH ring finger microconduit made earlier, and "give" (a slight sponginess) was detected. In the present experiment with Subject B's toenail, however, Subject B reported no sensation even when Subject A pressed harder. All of this together indicated that Subject B's toe nail was clearly thicker at the "nail-attached" site.

EXAMPLE 12

Nail 7

This experiment included formation of microconduits in the toe nails of Subject B, within infected regions that had thicker nail, and a demonstration of a condition for self-limiting of microconduit depth.

Materials and Methods: Prior to carrying out these experiments modifications were made to the nozzle holder, trying to make it easier to see the locus of the scission site by drilling view ports in the saddle. It was determined that the set up should be as before. Microparticle impingement was carried out for a longer time, until sensation was detected. It was decided to try some electrical resistance experiments. Those experiments were begun, and the following data on Subject B's RH foot, big toe, (site of the above-mentioned scission pit that was made several days earlier) was collected. (EKG electrode on bottom of the same big toe, the 0.006 inch diameter tungsten wire as a probe).

| PROBE | CONDITION | LOCATION | RESISTANCE |
|---|---|---|---|
| On toe skin | saline | ¼ inch behind nail | 19 kohm |
| On nail surface | dry | center of nail (clearly on bed) | 3.9-4 Megohm |
| Next to microconduit | saline | nail appears to be on bed | 7 Megohm |
| In microconduit | dry | nail appears to be on bed | 7 Megohm |
| In microconduit | saline | (within microconduit) | 7 Megohm |

Experimenter/subject = Subject A/Subject B

Results: The part of the nail attached to the bed had a lower resistance; the part of the nail that was lifted away from the bed had very high resistance.

The saddle/nozzle device to make a microconduit was set-up using the 25 psi, 85V flow setting, 0.030+inch nozzle to nail spacing. It was decided to scission for 40+seconds, or perhaps until sensation onset. The microparticle impingement was stopped at 75 seconds because of uncertainty regarding microconduit depth. There was indeed a microconduit, but there was evidence that the position of the saddle/nozzle device had moved, as one could see particulate-caused hazing and a depression in front of the hole. Upon examination, this non-nail penetrating microconduit was found to be deeper than the microconduit made a week ago. It was decided to form another microconduit.

An attempt was made to make the saddle/nozzle steadier this time, and to tip it forward over the toe, to make certain the nozzle was about perpendicular to the surface of the curved nail. In this experiment microparticles were locally impinged for 90 seconds before terminating. Presumably, the growing microconduit had not reached living tissue. Subject A probed the bottom of the microconduit with the "depth probe", and it felt hard. The marks on the depth probe indicated that the microconduit was 0.040 inch (1000 micrometers) deep. A saline electrical conductivity test was performed and the resistance was in the 7 Megohm range, indicating lots of nail left (i.e. the nail had not been penetrated by this microconduit).

EXAMPLE 13

Nail 9

The next experiment was for Subject B to control the particulate generator (modified S.S. White machine) and to time the scission duration, while Subject A held the saddle/nozzle arrangement firmly to his toe nail, to prevent any movement. Subject B terminated the experiment after 240 seconds. The microconduit was not through the nail. It measured a bit more than 0.040 inch (perhaps 0.045 inch) deep, was hard bottomed and sensationless according to Subject B.

The particulate size, particulate nozzle diameter, microconduit diameter are all believed to affect this self-limitation. It was decided that the next experiment should use the 0.018 inch nozzle instead of the 0.011 inch employed in all of these experiments. This would change the form factor from 0.022 inch diameter and 0.042 inch deep (2 to 1). Extrapolation of those numbers predicts that if the nozzle is 0.018 inch diameter, we would stall out at 0.036 inch diameter and 0.072 inch deep. Another microconduit was formed at a new site over a region attached to the nail bed.

Using the 0.018 nozzle, with the holding fixture firmly fixed to the nail, Subject B timed the period of scission, and could turn the particulate flow off.

Results: At 70 seconds, Subject B slightly detected sensation. At 80 seconds Subject B clearly felt mild sensation and stopped the particulate flow. Blood was clearly issuing from the microconduit, with no sensation. Based on impingement time, the microconduit depth was estimated as 0.060 inch.

The site was rinsed with deionized water and covered with cellophane tape. After three hours, Subject B reported sensation in that toe, and trimmed the nail overhang, the trimming stopping the sensation. There had been observable additional blood flow. The tape was removed two days later, with no further observable effects.

Subject A measured Subject B's toe nail overhang right in front of these sites. The toe nail thickness was in the range of 0.050-0.065 inch. In looking under his nails, there was a striated buildup of what appeared to be fungally-altered nail material. The middle toe on his right foot was the worst. The altered material ranged between 0.125 and 0.200 inch thick. Protruding grey/white regions of material are punky, but quite hard in compression.

EXAMPLE 14

Nail 10

This Experiment created a microconduit in the toe nail of Subject A and demonstrates 'nail piercing' to accommodate 'nail jewelry'.

Methods and Materials: The experiment was carried out on Subject B's right hand big toe nail. A location in the overhang of the nail, near a protruding mass of fungal-infected nail material and debris, measuring 0.060-0.090 inches thick was selected.

Results: Particulate impingement for 240 seconds created a microconduit through the nail. A piece of 0.005 inch tungsten wire was inserted through the microconduit, around the nail edge, and back through the microconduit, thus inventing nail jewelry. This decoration was duplicated with a piece of gold wire. This demonstrates 'nail piercing' for cosmetic reasons.

Also, Subject B demonstrated the use of a toe nail microconduit as a reservoir for drug-containing cream (Micronazole Nitrate Cream, USP 2% (E. Fugera & Co., Melville, N.Y.) by spreading the cream over the locus of the microconduit and wiping off the excess. This left a small 'white dot' that could easily be reloaded as desired.

Equivalents

While this invention has been particularly shown and described with references to certain embodiments thereof, it will be understood by those skilled in the art that various changes in form and details may be made therein without departing from the spirit and scope of the invention encompassed by the appended claims. Such equivalents are intended to be encompassed in the scope of the following claims.

REFERENCES

1. Smith, E. W. and Maibach, H. I., eds., Percutaneous Penetration Enhancers, (Boca Raton: CRC Press, 1995).

2. Schaefer, H. and Redelmeier, T. E., Skin Barrier: Principles of Percutaneous Absorption. (Basel: Karger, 1996).

3. Langer, R. "Drug delivery and targeting.," *Nature*, 392: S5-S1 (1998).

4. Elias, P. M., et al. "Percutaneous transport in relation to stratum corneum structure and lipid composition," *J. Invest. Dermatol.,*" 76:297-301 (1981).

5. Elias, P. M., and Menon, G. K., "Structural and lipid biochemical correlates of the epidermal permeability," *Adv. Lipid Res.*, 24:1-26 (1991).

6. Zewert, T. E., et al., "Creation of transdermal pathways for macromolecule transport by skin electroporation and a low toxicity, pathway-enlarging molecule," *Bioelectrochem. Bioenerget.*, 49:11-20 (1999).

7. Ilic, L., et al., "Electrochemical creation of microconduits in full-thickness human skin for transdermal drug delivery by pressure-driven flow," *Proc. Internat. Symp. on Controlled Release of Bioact. Materials, Controlled Release Society,* 26:178-179 (1999).

8. Ilic, L., et al., "Spatially constrained skin electroporation with sodium thiosulfate and urea creats transdermal microconduits," *J. Controlled Release,* 61:185-202 (1999).

9. Weaver, J. C., and Langer, R., "Electrochemical creation of large aqueous pathways: An approach to transdermal drug delivery," *Progress in Dermatology,* 33:1-10 (1999).

10. Yamashita, N. et al., "Scanning electron microscopic evaluation of the skin surface after ultrasound exposure," *The Anatomical Record,* 247:455-461, (1997).

11. Tachibana, K., and Tachibana, S., "Transdermal delivery of insulin by ultrasonic vibration," *J. Pharm. Pharmacol.,* 43:270-271, (1989).

12. Mitragotri, S., et al., "Ultrasound-mediated transdermal protein delivery," *Science,* 269:850-853 (1995).

13. Mitragotri, S., et al., "Determination of threshold energy dose for ultrasound-induced transdermal drug transport," *J. Controlled Release,* 63:41-52 (2000).

14. Jacques, S. L., et al., "Controlled removal of human stratum corneum by a pulsed laser," *J. Invest. Dermatol.,* 88:88-93 (1987).

15. Nelson, J. S., et al., "Mid-infrared laser ablation of stratum corneum enhances in vitro percutaeous transport of drugs," *J. Invest. Dermatol.,* 97:874-879 (1991).

16. Flock, S., et al., "Transdermal drug delivery with a TRANSMEDICA Er:YAG laser device," *Transmedica Technical Report*, (Mar. 1, 1997).

17. Longridge, D. J., et al.; "Effects of payload per unit area on dermal Powdeject™ delivery of testosterone to conscious rabbits," *Proc. Int'l Symp. Control. Rel. Bioact. Mater., Controlled Release Society,* 25:595-596 (1998).

18. Uchida, M. et al, "Transdermal microparticle delivery by a supersonic-helios™ gun system," *Proc. Int'l. Symp. Control. Rel. Bioact. Mater., Controlled Release Society,* 25:575-576 (1998).

19. Eisenbraun, M. D., et al., "Examination of parameters affecting the elicitation of humoral immune response by particle bombardment-mediated genetic immunization," *DNA and Cell Biology,* 12:791-797 (1993).

20. Macklin, M. D., et al., "Immunization of pigs with a particle-mediated DNA vaccine to influenza. A virus protects against challenge with homologous virus," *J. of Virology,* 72:1491-1496 (1998).

21. J. A. Eppstein, M. R. Hatch, and D. Yang. Microporation of human skin for drug delivery and monitoring applications. International Patent Application WO 97/07734.

22. McAllister, D., et al., "Microfabricated microneedles: A novel approach to transdermal drug delivery," *Control Release Society Program*, p. 20, (1998).

23. Henry, S., et al., "Fluorescein kinetics in interstitial fluid harvesting from diabetic skin during fluorescein angiography: Implications for monitoring," *Diabetes Tech. Therapeut.,* 1:21-27 (1999).

24. Smith, A., et al, "Fluorescein kinetics in interstitial fluid harvesting from diabetic skin during fluorescein angiography: implications for glucose monitoring," *Diabetes Tech. Therapeut.*, 1:21-27 (1999).

25. Lee, S., et al., "Laser stress waves induce transient increase of the stratum corneum permeability: Implications for transdermal drug delivery," *J. Invest. Dermatol.*, 108:786 (1997).

26. Cullander, C., "What are the pathways of iontophoretic current flow through mammalian skin?" *Adv. Drug Delivery Rev.*, 9:119-135 (1992).

27. Inada, H., et al., "Studies of the effects of applied voltage and duration on human epidermal membrane alteration/recovery and the resultant effects upon iontophoresis," *Pharm. Res.*, 11:687-697 (1994).

28. Sage, B. H., "Percutaneous penetration enhancers." In Iontophoresis, (Boca Raton: CRC Press), pp. 351-368 (1995).

29. Green, P. G., "Iontophoretic delivery of peptide drugs," *J. Controlled Release*, 41:33-48 (1996).

30. Merino, V., et al., "Transdermal therapy and diagnosis by iontophoresis," *Trends in Biotechnology*, 15:288-290 (1997).

31. Dinh, S. M., et al., "Upper and lower limits of human skin electrical resistance in iontophoresis," *AIChE J.*, 39:2011-2018 (1993).

32. Scott, E. R., et al., "Direct imaging of ionic pathways in stratum corneum using scanning electrochemical microscopy," *Solid State Ionics*, 53-56:176-183 (1992).

33. Monteiro-Riviere, N. A., et al., "Identification of the pathway of iontophoretic drug delivery: Light and ultrastructure studies using mercuric chloride in pigs," *Pharm. Res.*, 11:251-256(1994).

34. Langkjaer, L., et al., "Iontophoresis of monomeric insulin analogues in vitro: Effects of insulin charge and skin pretreatment," *J. Controlled Release*, 51:47-56 (1998).

35. Chizmadzhev, Y., et al., "Electrical properties of skin at moderate voltages: Contribution of appendageal macropores," *Biophysical, J.*, 74:843-856 (1998).

36. Prausnitz, M. R., et al., "Electroporation of mammalian skin: A mechanism to enhance transdermal drug delivery," *Proc. Nat. Acad. Sci.*, 90:10504-10508 (1993).

37. M. R. Prausnitz, D. S. Seddick, A. A. Kon, V. G. Bose, S. Frankenburg, S. N. Klaus, R. Langer, and J. C. Weaver. Methods for in vivo tissue electroporation using surface electrodes. *Drug Delivery*, 1: 125-131, 1993.

38. S. A. Gallo, A. R. Oseroff, P. G. Johnson, and S. W. Hui. Characterization of electric-pulse-induced permeabilization of procine skin using surface electrodes. *Biophysical Journal*, 72:2805-2811, 1997.

39. R. Vanbever, D. Fouchard, A. Jadoul, N. DeMorre, V. Preat, and J-P Marty. In vivo noninvasive evaluation of hairless rat skin after high-voltage pulse exposure. *Skin Parmacol. Appl. Skin Physiol.*, 11:23-34, 1998.

40. R. Vanbever, G. Langers, S. Montmayeur, and V. Preat, Transdermal delivery of fentanyl: Rapid onset of analgesia using skin electroporation. *J. Controlled Release*, 50:225-235, 1998.

41. T. Chen, R. Langer, and J. C. Weaver. Skin electroporation causes molecular transport across the stratum corneum through local transport regions. *J. Invest. Dermatol. Symposium Proceedings*, 3:159-165, 1998.

42. T. Chen, E. M. Segall, R. Langer, and J. C. Weaver. Skin electroporation: Rapid measurements of the transdermal voltage and flux of four fluorescent molecules show a transition to large fluxes near 50 V for 1 ms pulses. *J. Pharmaceutical Sciences*, 87:1368-1374, 1998.

43. R. VanBever, U. F. Pliquett, V. Preat, and J. C. Weaver. Comparison of the effects of short, high-voltage and long, medium-voltage pulses on skin electrical and transport properties. *J. Controlled Release*, 60:3 5-47, 1999.

44. T. E. Zewert, U. F. Pliquett, R. Langer, and J. C. Weaver. Transdermal transport of DNA antisense oligonucleotides by electroporation. *Biochim. Biophy. Res. Comm.*, 212:286-292, 1995.

45. M. R. Prausnitz, E. R. Edelman, J. A. Gimm, R. Langer, and J. C. Weaver. Transdermal delivery of heparin by skin electroporation. *Bio/Technology*, 13:1205-1208, 1995.

46. J. C. Weaver, T. E. Zewert, U. Pliquett, R. Vanbever, M. R. Prausnitz, T. Chen, C. Cullendar, R. Guy, and R. S. Langer. Introduction of modifying agents into skin by electroporation. U.S. Pat. No. 5,911,223.

47. J. C. Weaver, T. E. Zewert, U. F. Pliquett, R. Vanbever, T. R. Gowrishankar, T. O. Herndon, G. T. Martin, T. E. Vaughan, L. Ilic, J. Handwerker, T. Chen, D. Allen, R. Langer, and N. Monteiro-Riviere. Proceedings of the 6th conference on perspectives in percutaneous penetration. Chapter Pathway-Enlarging Molecules for Skin Electroporation: The Possibility of Macromolecule Delivery with Minimal Side Effects, 2000.

48. J. C. Weaver, U. Pliquett, and T. E. Vaughan. Apparatus and method for electroporation of tissue. U.S. Pat. No. 5,983, 131.

49. H. M. Heise. Non-invasive monitoring of metabolites using near infrared spectroscopy: State of the art. *Horm. Metab. Res.*, 28:527-534, 1996.

50. U. Fischer, R. Ertle, P. Abel, K. Rebrin, and G. Katsch. Assessment of subcutaneous glucose concentration: Validation of the wick technique as a reference for implanted electrochemical sensors in normal and diabetic dogs. *Diabetologia*, 30:940-945, 1987.

51. K. M. Quan, G. B. Christison, H. A. MacKenzie, and P. Hodgson. Glucose determination by a pulse photoacoustic technique: An experimental study using a gelatin-based tissue phantom. *Phys. Med. Biol.*, 38:1911-1922, 1993.

52. J. A. Tamada, N. J. V. Bomannon, and R. O. Potts. Measurement of glucose in diabetic subjects using noninvasive transdermal extraction. *Nature Medicine*, 1:1198-1202, 1995.

53. N. Ito, A. Saito, S. Kayashima, J. Kimura, T. Kriyama, N. Nagata, T. Arai, and M. Kikuchi. Transcutaneous blood glucose monitoring system based on ISFET glucose sensor and studies on diabetic patients. *Front. Med. Biol. Eng.*, 6:269-280, 1995.

54. A. J. Berger, K. Itzkan, and M. S. Feld. Feasibility of measuring blood glucose concentration by near-infrared Raman spectroscopy. *Spectochim. Acta*, 53:2887-2292, 1997.

What is claimed is:

1. A method of modifying or manipulating body tissue by forming at least one microconduit therein, comprising the steps of:

a) accelerating a plurality of microparticles to a velocity that causes the microparticles to penetrate a region of a tissue surface upon impingement of the microparticles on the tissue surface;

b) directing the microparticles towards the region of tissue surface, thereby causing the microparticles to penetrate the tissue; and c) scissioning the tissue with the impinging microparticles, thereby forming a plurality of free microtissue particles, and thereby forming a microconduit;

d) using said microconduit for manipulation or modification of the body tissue in a manner selected from the group consisting of:

(i) extracting an analyte from the body tissue by removing the analyte from the tissue through the microconduit;

(ii) forming a molecular matrix within at least one microconduit in body tissue by directing a molecular matrix into the microconduit;

(iii) making at least one biopotential measurement across the body tissue by placing at least two electrodes in electrical connection with the body tissue with at least one electrode at the microconduit; and making a biopotential measurement across the electrodes;

(iv) delivering at least one stored molecule to the body tissue by storing the molecule in at least one puncturable capsule in proximity to at least one microconduit;

(v) reducing pressure caused by a pool of blood beneath an injured or traumatized portion of body tissue by releasing the pressure through the microconduit;

(vi) piercing the body tissue for a decorative purpose by inserting at least one wire through one or more microconduits;

(vii) marking the body tissue with at least one identifying mark or at least one decorative mark by directing a dye or an ink into at least one microconduit;

(viii) treating an infection below the surface of the body tissue by administering at least one therapeutic molecule or ion by directing the therapeutic molecule or ion into at least one microconduit, thereby delivering the therapeutic molecule or ion through the surface of the body tissue;

(ix) removing hair from the surface of the body tissue by forming one or more microconduits at or near the hair follicles on the body tissue, followed by washing with water, thereby removing the hair from the body tissue; and (x) implanting hair into the surface of the body tissue by forming one or more microconduits having a diameter and depth sufficient to serve as a new hair follicle on the body tissue, followed by implantation of a live hair follicle into the microconduits.

2. The method of claim 1, wherein the body tissue is skin or nail tissue.

3. The method of claim 1, wherein the manipulation or modification of the body tissue comprises extracting an analyte from a tissue, wherein analyte is removed from the tissue through the microconduit.

4. The method of claim 3, wherein the analyte is removed by sampling or by reducing pressure over the microconduit.

5. The method of claim 3, further comprising the step of measuring the amount of analyte while the analyte is within the microconduit.

6. The method of claim 5, wherein the tissue is skin.

7. The method of claim 3, wherein the tissue is skin.

8. The method of claim 1, wherein the manipulation or modification of the body tissue comprises forming a molecular matrix within at least one microconduit, wherein the molecular matrix is formed within the microconduit by directing a molecular matrix into the microconduit.

9. The method of claim 8, wherein the molecular matrix is a gel.

10. The method of claim 9, wherein the gel is calcium alginate.

11. The method of claim 9, wherein the molecular matrix is a polymer matrix.

12. The method of claim 1, wherein the manipulation or modification of the body tissue comprises making at least one biopotential measurement across the skin, by placing at least two electrodes in electrical connection with the skin with at least one electrode at the microconduit; and making a biopotential measurement across the skin.

13. The method of claim 12, wherein the biopotential measurement is an electrocardiogram.

14. The method of claim 13, wherein the electrocardiogram measurement is obtained during exercise stress testing.

15. The method of claim 12, wherein the biopotential measurement is an electromyogram.

16. The method of claim 12, wherein the biopotential measurement made is suitable for neuromuscular testing.

17. The method of claim 12, wherein the biopotential measurement is an electroencephalogram to monitor anesthesia.

18. The method of claim 1, wherein the manipulation or modification of the body tissue comprises delivering at least one molecule to tissue within microconduit, comprising the step of storing the molecule in at least one puncturable capsule in proximity to at least one microconduit, and puncturing said capsule to release one or more molecules into said microconduit.

19. The method of claim 18, wherein the stored molecule includes a therapeutic molecule or ion.

20. The method of claim 19, wherein the body tissue is nail tissue.

21. The method of claim 1, wherein using said microconduit for manipulation or modification of the body tissue comprises forming at least one microconduit through nail tissue, comprising the steps of:

a) accelerating a plurality of microparticles to a velocity that causes the microparticles to penetrate a region of nail tissue surface upon impingement of the microparticles on the nail tissue surface;

b) directing the microparticles towards the region of nail tissue surface, thereby causing the microparticles to penetrate the nail tissue surface; and c) scissioning the nail tissue with the impinging microparticles, thereby forming a plurality of free nail microtissue particles, and thereby forming a microconduit through the nail tissue.

22. The method of claim 1, wherein using said microconduit for manipulation or modification of the body tissue comprises a method for treating an infection of tissue underlying nail tissue, comprising the steps of:

a) accelerating a plurality of microparticles to a velocity that causes the microparticles to penetrate a region of nail tissue surface upon impingement of the microparticle on the nail tissue surface;

b) directing the microparticles towards the region of nail tissue surface, thereby causing the microparticles to penetrate the nail tissue surface;

c) scissioning the nail tissue with the impinging microparticles, thereby forming a plurality of free nail microtissue particles, and thereby forming a microconduit through the nail tissue; and d) administering at least one therapeutic molecule or ion by directing the therapeutic molecule or ion into at least one microconduit, thereby delivering the therapeutic molecule or ion through the nail tissue.

23. The method of claim 1, wherein the manipulation or modification of the body tissue comprises a method for marking nail tissue with at least one identifying mark or at least one decorative mark, comprising the steps of:

a) accelerating a plurality of microparticles to a velocity that causes the microparticles to partially penetrate into a region of nail tissue surface upon impingement of the microparticles on the nail tissue surface;

b) directing the microparticles towards the region of nail tissue surface, thereby causing the microparticles to partially penetrate the nail tissue surface and form a microconduit in the nail tissue; and c) scissioning the nail tissue with the impinging microparticles, thereby forming a plurality of free nail microtissue particles, and thereby forming a microconduit through the nail tissue; and d) directing a dye or an ink into at least one microconduit, thereby marking the nail tissue.

24. The method of claim 1, wherein the manipulation or modification of the body tissue comprises a method for inserting at least one wire through at least one microconduit, comprising the steps of:

a) accelerating a plurality of microparticles to a velocity that causes the microparticles to penetrate a region of nail tissue surface upon impingement of the microparticles on the nail tissue surface;

b) directing the microparticles towards the region of nail tissue surface that extends beyond the body, thereby causing the microparticles to penetrate the nail tissue surface;

c) scissioning the nail tissue with the impinging microparticles, thereby forming a plurality of free nail microtissue particles, and thereby forming a microconduit through the nail tissue; and d) directing a wire into at least one microconduit, thereby inserting the wire through the microconduit.

25. The method of claim 1, wherein the manipulation or modification of the body tissue comprises a method of reducing a pressure caused by a pool of blood beneath an injured or traumatized nail comprising the steps of:

a) accelerating a plurality of microparticles to a velocity that causes the microparticles to penetrate a region of nail tissue surface upon impingement of the microparticles on the nail tissue surface;

b) directing the microparticles towards the region of nail tissue surface, thereby causing the microparticles to penetrate the nail tissue surface;

c) scissioning the nail tissue with the impinging microparticles, thereby forming a plurality of free nail microtissue particles, and thereby forming a microconduit through the nail tissue; and d) thereby releasing the pressure through the microconduit.

26. The method of claim 1, wherein accelerating a plurality of microparticles further comprises accelerating a plurality of microparticles to a velocity that is approximately in the range of one meter per second.

* * * * *

UNITED STATES PATENT AND TRADEMARK OFFICE
CERTIFICATE OF CORRECTION

PATENT NO. : 7,597,692 B2
APPLICATION NO. : 10/800587
DATED : October 6, 2009
INVENTOR(S) : Weaver et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1383 days.

Signed and Sealed this

Twenty-eighth Day of September, 2010

David J. Kappos
*Director of the United States Patent and Trademark Office*